(12) United States Patent
Rousso et al.

(10) Patent No.: US 8,406,864 B2
(45) Date of Patent: Mar. 26, 2013

(54) ASSESSING CARDIAC ACTIVITY

(75) Inventors: Benny Rousso, Rishon-LeZion (IL);
Eyal Lebanony, Haifa (IL); David Prutchi, Voorhees, NJ (US); Ophir Bitton, Zikhron-Yaakov (IL)

(73) Assignee: Impulse Dynamics NV, Curacao (AN)

( * ) Notice: Subject to any disclaimer, the term of this patent is extended or adjusted under 35 U.S.C. 154(b) by 1150 days.

(21) Appl. No.: 12/223,651

(22) PCT Filed: Feb. 4, 2007

(86) PCT No.: PCT/IL2007/000141
§ 371 (c)(1),
(2), (4) Date: Aug. 6, 2008

(87) PCT Pub. No.: WO2007/091244
PCT Pub. Date: Aug. 16, 2007

(65) Prior Publication Data
US 2009/0030471 A1    Jan. 29, 2009

Related U.S. Application Data

(60) Provisional application No. 60/765,974, filed on Feb. 7, 2006.

(51) Int. Cl.
*A61N 1/36* (2006.01)
(52) U.S. Cl. .......... 600/523; 600/509; 600/517; 600/521
(58) Field of Classification Search .......... 600/508–509, 600/517, 521, 523
See application file for complete search history.

(56) References Cited

U.S. PATENT DOCUMENTS

| | | | | |
|---|---|---|---|---|
| 4,733,667 A | * | 3/1988 | Olive et al. | 607/24 |
| 6,643,548 B1 | | 11/2003 | Mai et al. | |
| 7,286,871 B2 | * | 10/2007 | Cohen | 600/544 |
| 2004/0059237 A1 | * | 3/2004 | Narayan et al. | 600/509 |

FOREIGN PATENT DOCUMENTS

| | | |
|---|---|---|
| EP | 0459539 | 12/1991 |
| EP | 0503839 | 9/1992 |
| GB | 2070282 | 9/1981 |
| WO | WO 01/13992 | 3/2001 |
| WO | WO 0130436 A2 * | 5/2001 |
| WO | WO 2005/018737 | 3/2005 |
| WO | WO 2005/118056 | 12/2005 |
| WO | WO 2007/091244 | 8/2007 |

OTHER PUBLICATIONS

International Search Report Dated May 23, 2007 From the International Searching Authority Re.: Application No. PCT/IL2007/000141.
Written Opinion Dated May 23, 2007 From the International Searching Authority Re.: Application No. PCT/IL2007/000141.
International Preliminary Report on Patentability Dated Aug. 21, 2008 From the International Bureau of WIPO Re.: Application No. PCT/IL2007/000141.

* cited by examiner

*Primary Examiner* — Rex R Holmes

(57) ABSTRACT

A method of assessing contractility of a cardiac muscle which has at least one activation parameter, the method comprising: (a) utilizing time correlated data pertaining to at least one activation parameter to produce a profile of said parameter; (b) identifying from measurement of said at least one parameter a time interval during which interference from an artificial signal occurs; (c) ameliorating effects of said interference; and (d) analyzing changes in said profile to generate an indication of contractility, as a function of time to generate a cardiac activation profile.

49 Claims, 12 Drawing Sheets

1b  2082005(110724) — TIMING LS TO MAXZ

ASSESSING CARDIAC ACTIVITY

RELATED APPLICATIONS

This application is a National Phase of PCT Patent Application No. PCT/IL2007/000141 having International filing date of Feb. 4, 2007, which claims the benefit of 35 USC §119(e) of U.S. Provisional Patent Application No. 60/765,974 filed on Feb. 7, 2006. The contents of the above Applications are all incorporated herein by reference.

FIELD OF THE INVENTION

The present invention relates to assessing cardiac activity, for example, changes relating to contractility.

BACKGROUND OF THE INVENTION

Cardiac contractility modulation (CCM) is known as a method of improving heart function. CCM relies upon application of an electric signal to a selected portion of the heart to increase strength of a subsequent contraction initiated by a cardiac signal generated by the heart and/or a signal supplied by a conventional pacemaker.

In order to assess efficacy of CCM, pressure measurements within the heart are typically used to directly assess cardiac contractility. For example, Left Ventricular Pressure (LVP) may be measured directly by LV catheters such as those produced by Millar. Pressure measurements within the heart typically include implantation of a measuring device (e.g. Millar catheter) within one of the heart chambers. Implantation is an invasive procedure, most often involving introducing a catheter to a femoral artery and guiding the measuring device to a heart chamber. As a result, direct pressure measurements are not widely employed to identify patients who are candidates for CCM. Because leaving the catheter and measuring device in the patient for an extended period of time is impractical, direct measurements of cardiac pressure are also not widely used for periodic monitoring of patients in whom a CCM device has been implanted.

In order to circumvent the need to measure pressure directly, attempts have been made to gauge cardiac mechanical parameters such as stroke volume using measurements of electrical impedance between two leads. For a given current flowing between the two leads, the impedance will be influenced by distance and/or material between the two leads. In that context, Pressure-Volume catheters were developed with respective analysis systems that evaluate P-V loops (e.g. the DF series of catheters manufactured by CD-Leycom, Zoetermeer, Netherlands). These devices also require implantation of a catheter within a heart chamber.

Cambridge Heart (Bedford Mass., USA) markets a system for analysis of T-wave alternance as a means of gauging stability of a heartbeat. The Cambridge Heart Microvolt T-Wave Alternans (http://www.cambridgeheart.com/) Test measures beat-to-beat fluctuations in a person's heartbeat. T-wave alternans indicates heartbeat variations, measured at one millionth of a volt. Detection is from sensors on a patient's chest.

A wide range of published clinical data has shown that patients with symptoms of or at risk of life threatening arrhythmias who have a normal or negative Microvolt T-Wave Alternance (MTWA) test are at minimal risk for a sudden cardiac event while those who have an abnormal or positive test are at increased risk for subsequent sudden cardiac events including sudden death.

Use of intracardiac impedance measurements has been correlated to cardiac contractility since the 1950s and is currently used successfully as a clinical sensor in permanent pacemakers (M. Schaldach, "Electrotherapy of the Heart", Chapter on Cardiac Control Parameters, pp 105-143, Berlin: Springer-Verlag 1992; J. G. Webster, "Design of Cardiac Pacemakers", Chapter 16, pp 369-396, IEEE Press 1995 and W. Arthur and G. C. Kaye, "Clinical Use of Intracardiac Impedance: Current Applications and Future Perspectives", JOURNAL OF PACING AND CLINICAL ELECTROPHYSIOLOGY, Volume 24, No. 4, Part 1, April 2001; These three articles fully incorporated herein by reference). Impedance measurements may be used to ascertain, the pre-ejection period (PEP) also known as the pre-ejection interval (PEI) and/or a ventricular inotropic parameter (VIP). In general a short PEP is indicative of a robust contraction. The VIP also indicates the strength of contraction. The VIP has less patient to patient variance than the PEP. Measurement of PEP and/or VIP typically employs leads deployed in the heart chambers.

Cardiac function may also be assessed acoustically. A cardiac acoustic profile is called a phonocardiogram (PCG) and indicates blood flow turbulence. Researchers usually distinguish two basic patterns of heart sound S1 and S2. ("Hemodynamic Pressure Instabilities and their Relation to Heart Ausculation". Vladimir Kudriavtsev, Vladimir Polyschuk, Olga Saynina. Proceeding of ASME PVP Division Conference: 5$^{th}$ international Symposium on Computational Technologies for Fluid/Thermal/Chemical/Stressed Systems with Industrial Applications Jul. 25-29, 2004, San Diego/La Jolla, USA; http://www.bsignetics.com/news.htm). This paper is fully incorporated herein by reference. Acoustic profiles may be generated by non-invasive means and have been previously employed to evaluate electrical activity of the heart.

SUMMARY OF THE INVENTION

An aspect of some embodiments of the present invention relates to estimating the effect of an applied electrical signal on cardiac contractility. Contractility may be assessed directly (e.g. by measuring intra-cardiac pressure) or indirectly (e.g. by measuring an acoustic signal, or a local impedance). Optionally, the applied electric signal is a CCM signal. In an exemplary embodiment of the invention, analysis of the first derivative of a measured parameter as a function of time provides information about the effect on contractility of the applied electrical signal.

An aspect of some embodiments of the present invention relates to a method of assessing contractility of a cardiac muscle, the method comprising analyzing changes in an activation profile of the heart. Optionally, the activation profile is a mechanical activation profile. In an exemplary embodiment of the invention, the measurement is an indirect measurement which correlates to a mechanical activity. Optionally, the measurement includes measuring changes in timing of cardiac mechanical or electrical activities. In an exemplary embodiment of the invention, the timing is estimated using one or more of measuring of cardiac acoustics, local cardiac impedance and/or internal electrical signal and/or cardiac acceleration.

In an exemplary embodiment of the invention, analysis of a rate of change of a measured parameter with respect to time indicates a degree of contractility.

An aspect of some embodiments of the present invention relates to, reducing the effects of measurement artifacts (e.g. those produced by an electric stimulus) on the data analysis reduced. Optionally, artifacts are blanked out and/or data is recovered by calculation. Optionally, impedance measurements are absolute. Absolute measurement in this context means that the measurements are not calibrated in any specific units and are relative only to one another. In an exemplary embodiment of the invention, impedance measurement and electrical sensing provide an estimate of cardiac contractility.

In an exemplary embodiment of the invention, the measurements of the cardiac activation are not calibrated. Optionally, the measurement comprises detecting changes in timing between occurrence of two or more events.

In an exemplary embodiment of the invention, the measurements take into account a disruptive effect of a CCM signal on the measurements. Optionally, signals acquired at a time of application of CCM are blanked.

Optionally, CCM delivery circuitry and measurement circuitry are adapted to function cooperatively and/or may exchange information between them. For example, exact timing of CCM delivery can be provided by CCM delivery circuitry to measurement circuitry. In an exemplary embodiment of the invention, provision of information on CCM timing permits measurement circuitry to identify CCM artifacts and take the artifacts into account, for example by excluding them from calculations or blanking the artifact signals.

In some embodiments of the invention delivery of the CCM signal may be changed to facilitate the measurements. This may take the form of one or more of changing the time of activation, the amplitude and/or frequency of an activation signal and/or its duty cycle. Alternatively or additionally, it may include activation of less than all electrodes normally used for activation and/or activation only on some heartbeats.

In an exemplary embodiment of the invention, CCM delivery circuitry and measurement circuitry are integrated into a single unit.

In exemplary embodiments of the invention, CCM delivery circuitry and measurement circuitry may each be implemented in an implantable configuration or an external configuration. Optionally, no implanted leads are employed.

An aspect of some embodiments of the present invention relates to a profile of activation values as a function of time and corresponding non-excitatory signal (e.g. CCM or Cardiac Contractility Modulation) delivery parameters. In an exemplary embodiment of the invention, efficacy of a CCM device and/or CCM signal is evaluated based on this profile. For purposes of this specification and the accompanying claims, "non-excitatory signal delivery" includes the application or input of one or more non-excitatory signals defined in terms of one or more of electrical parameters (e.g. pulse magnitude and/or duration) and/or delivery pattern (e.g. electrode placement and/or spacing) and/or temporal parameters (e.g. time lapse between pulses). Optionally, the non-excitatory signal is directed towards reducing an arrhythmia. In an exemplary embodiment of the invention, reduction and/or elimination of an arrhythmia contributes to an improvement in cardiac contractility. In an exemplary embodiment of the invention, an improvement in a contractility parameter is considered indicative of a success in arrhythmia intervention. Optionally, a delivered CCM signal includes both non-excitatory and excitatory components.

An aspect of some embodiments of the present invention relates to evaluating a position of a lead by analyzing a change in a cardiac activation parameter profile resulting from a signal applied through the lead. Optionally, the signal is a pacing signal and/or a CCM signal. In various exemplary embodiments of the invention, the lead is employed as a CCM lead and/or a pacing lead and/or a measuring lead after the position evaluation and possible adjustment of position based on the evaluation.

In an exemplary embodiment of the invention, there is provided a method of assessing contractility of a cardiac muscle which has an activation parameter, the method comprising:
(a) utilizing time correlated data pertaining to an activation parameter to produce a profile of said parameter; and
(b) analyzing changes in said profile to generate an indication of contractility.

Optionally, the activation parameter includes a mechanical activation parameter.

Optionally, the mechanical activation parameter includes impedance.

Optionally, the mechanical activation parameter includes acoustic output.

Optionally, analyzing said changes includes analyzing changes in a first derivative of the profile.

Optionally, the time correlated data is acquired without any intra-corporeal measuring device.

In an exemplary embodiment of the invention, there is provided a method of assessing efficacy of a treatment on cardiac contractility, the method comprising:
(a) performing a method according to claim 2 to generate a first profile;
(b) applying a treatment and re-performing a method according to claim 2 to generate a second profile;
(c) comparing said first profile and said second profile to ascertain an efficacy of the treatment.

Optionally, the treatment includes administration of a cardiac contractility modulation (CCM) input.

In an exemplary embodiment of the invention, there is provided a system for assessing efficacy of a cardiac contractility modulation (CCM) device, the system comprising a data collection component designed and configured to utilize activation values correlated to time and corresponding CCM delivery values.

Optionally, the activation values reflect mechanical activation.

Optionally, the activation values reflect impedance.

Optionally, the activation values reflect acoustic data.

Optionally, the system includes data analysis circuitry designed and configured to analyze said activation values correlated to time and said corresponding CCM delivery values.

Optionally, the data analysis circuitry provides an output in the form of a desired change in activation profile.

Optionally, the analysis circuitry provides an output in the form of a recommended change in CCM delivery.

Optionally, the data analysis circuitry communicates with a controller which implements the recommended change in CCM delivery.

Optionally, the system includes a display adapted to display said activation values correlated to time as an activation profile.

In an exemplary embodiment of the invention, there is provided a method for evaluating a position of a lead, the method comprising,
(a) utilizing time correlated data pertaining to an activation parameter of a heart to produce a profile of said parameter;
(b) applying a signal through a lead at a position in said heart at a known time; and
(c) determining if said position of said lead is a desired position by analyzing a change in said profile resulting from the signal.

Optionally, an absence of a significant narrowing of a selected portion of said profile indicates that said position is an unfavorable position.

Optionally, a significant narrowing in said profile indicates that said position is said desired position.

Optionally, the signal is a pacing signal.

In an exemplary embodiment of the invention, there is provided a method for assessing efficacy of a protocol to modify cardiac contractility, the method comprising:

(a) administering a protocol to modify cardiac contractility;
(b) utilizing time correlated data pertaining to an activation parameter of a heart to produce a profile of said parameter to determine a post-protocol contractility status;
(c) evaluating said time correlated data pertaining to an activation parameter to determine an efficacy of said protocol.

Optionally, the method includes additionally utilizing time correlated data pertaining to an activation parameter of a heart to determine a pre-protocol contractility status;
wherein said evaluating includes comparison of said pre-protocol and said post-protocol contractility status.

Optionally, the method includes additionally utilizing time correlated data pertaining to an activation parameter of a heart in a plurality of subjects to determine a normative contractility status;
wherein said evaluating includes comparison of said normative and said post-protocol contractility status.

Optionally, the time correlated data reflect mechanical activation.

Optionally, the time correlated data include impedance data.

Optionally, the time correlated data include passive acoustic data.

Optionally, the evaluating indicates a desired change in activation profile which has not yet been achieved.

Optionally, the evaluating indicates a recommended change in CCM delivery.

In an exemplary embodiment of the invention, there is provided a method of generating a profile of the heart, the method comprising:

(a) measuring at least one parameter as a function of time to generate a cardiac activation profile;
(b) identifying a time interval during which interference from an artificial signal occurs; and
(c) ameliorating effects of said interference.

Optionally, the amelioration includes data deletion followed by interpolation to reconstruct a missing portion of said profile.

Optionally, the amelioration includes data deletion followed by data regeneration to reconstruct a missing portion of said profile.

Optionally, the amelioration includes calculation of a first derivative of said function.

Optionally, the amelioration includes application of a band pass filter.

In an exemplary embodiment of the invention, there is provided a method of assessing an effect of a non excitatory electric therapy, the method comprising:

(a) utilizing time correlated data pertaining to an activation parameter to produce a profile of said parameter; and
(b) analyzing changes in said profile to generate an indication of therapy efficacy.

Optionally, said activation parameter includes a mechanical activation parameter.

Optionally, the non-excitatory electric therapy includes CCM.

Optionally, the method comprises:
(a) performing the above method to generate a first profile;
(b) applying a treatment and re-performing the above method to generate a second profile;
(c) comparing said first profile and said second profile to ascertain an efficacy of the non excitatory electric treatment.

In an exemplary embodiment of the invention, there is provided a method of assessing cardiac disease status in a subject, the method comprising:
(a) utilizing time correlated data pertaining to an activation parameter to produce a profile of said parameter; and
(b) analyzing changes in said profile to generate an indication of cardiac contractility.

Optionally, said activation parameter includes a mechanical activation parameter.

Optionally, the method comprises:
(a) performing the above method generate a first profile;
(b) allowing an increment of time to elapse and re-performing the above method to generate a second profile;
(c) comparing said first profile and said second profile to ascertain a degree of disease progression.

BRIEF DESCRIPTION OF DRAWINGS

In the Figs., identical structures, elements or parts that appear in more than one Fig. are generally labeled with the same numeral in all the Figs. in which they appear. Dimensions of components and features shown in the Figs. are chosen for convenience and clarity of presentation and are not necessarily shown to scale. The Figs. are listed below.

DETAILED DESCRIPTION OF EXEMPLARY EMBODIMENTS

Overview

Following a brief description of a method and apparatus for contractility change determination, a range of various particular measures and signal processing methods and/or applications are described below.

Figure 1:
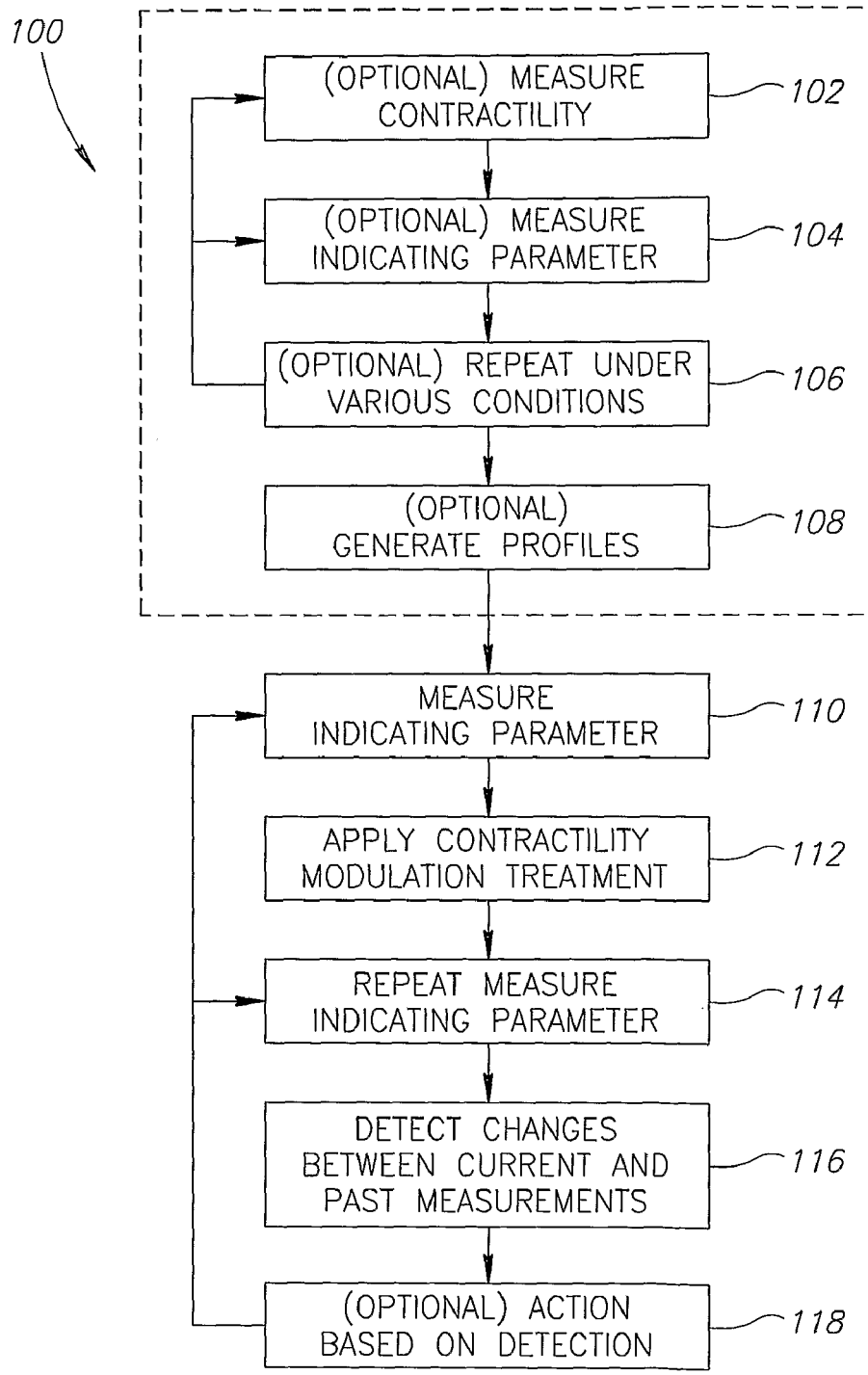
FIG. 1 is a flowchart of a method of contractility assessment, in accordance with an exemplary embodiment of the invention.

FIG. 1 is a flowchart of a method 100 of estimating the effect on cardiac contractility of a CCM signal (or other source of change).

In an optional calibration step, a correlation is found between contractility and another measure (such as impedance, acceleration or acoustics).

At 102, contractility is optionally measured directly, for example by using a Millar catheter. At 104, a parameter expected to indicate contractility indirectly is optionally measured. Various exemplary parameters suitable for indirect measures of contractility are explained in detail hereinbelow. Optionally, these measurements cover a significant portion of a cardiac cycle, for example, 30%, 50%, 80% or more and have a sampling rate of, for example, every 50 ms, every 10 ms, every 5 ms, or greater or lesser or intermediate values. The sampling rate may be non-uniform.

At 106, the measurements of contractility and/or the indicative parameter are optionally repeated under varying conditions, for example, different heart rates, and different heart disease states. In an exemplary embodiment of the invention, repetition under various conditions may indicate repetition of measurements on the same patient under different states of activity, for example prone, seated and walking on a treadmill at 2.5 Km/hour. Alternatively or additionally, repetition under various conditions may indicate with and without a pacing signal and/or employing different pacing signals. Optionally, two or more parameters expected to indicate contractility indirectly are employed either sequentially or concurrently.

At 108, one or more profiles of the indicative parameter as a function of contractility and/or contractility change are optionally generated. For example, a profile can indicate that in a normal heart, a change in contractility for the better is associated an earlier occurrence of valve opening in the left ventricle relative to the length of the contraction cycle as a whole. In another example, a pattern of impedance changes between two or more leads over an entire cardiac cycle (or at least 40% thereof) is correlated to contractility in the same patient.

Optionally, data from a large number of patients concerning 102, 104, 106 and/or 108 is gathered and stored in a database. In an exemplary embodiment of the invention, the database facilitates generation of defined relationships between indicative parameters and contractility so that these measurements do not need to be repeated for future patients.

Once a relationship between at least one indicating parameter and contractility has been established, whether for an individual patient, or by means of accumulated data in a data base, the indicating parameter (e.g. impedance between two leads) is measured 110. In an exemplary embodiment of the invention, measurement continues for at least 40% of a cardiac cycle, optionally through an entire cardiac cycle, optionally through 2 to 5 cardiac cycles, optionally through 6 to 10 cardiac cycles or more.

Application of a contractility modifying signal 112 is optionally conducted. A repeated measurement 114 of the same indicative parameter is optionally made after the contractility modifying signal has been applied. The contractility modifying signal may be, for example, a CCM signal.

At 116, the measurements of 114 are compared to those of 110 and/or to a previously generated profile (108) to estimate a change in mechanical activation profile and/or contractility.

At 118, an action is optionally taken based on a detection or lack of detection of a change in contractility. For example, if the indicative parameter is the pre ejection period (PEP; normal range=66 to 120 milliseconds); measurement 110 indicates 160 milliseconds and measurement 114 indicates 138 milliseconds, action 118 might be to increase the strength of the CCM signal applied at 112.

Figure 2:
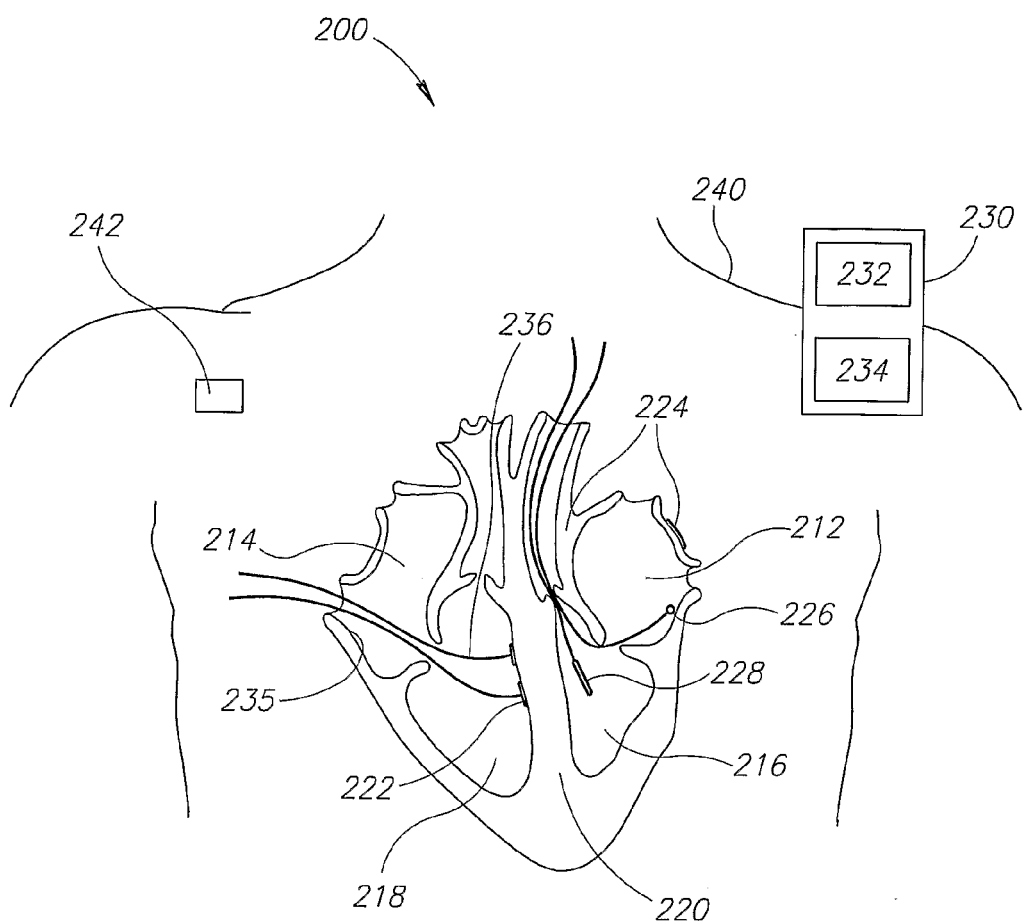
FIG. 2 is a schematic diagram showing measuring and/or CCM apparatus, in situ, in accordance with an exemplary embodiment of the invention.

Referring now to FIG. 2, an exemplary measuring system 200, and variants thereof, according to some embodiments of the present invention, is described. A heart, including left atrium 212, right atrium 214, left ventricle 216, right ventricle 218 and ventricular septum 220 is depicted inside body contour 240. System 200 may be employed, for example, to diagnose deviations from desired cardiac contractility and/or to exercise control over a correction mechanism for cardiac contractility. The correction mechanism may be, for example, a CCM mechanism and/or a conventional pacemaker.

In an exemplary embodiment of the invention, system 200 monitors cardiac contractility indirectly or directly. Direct measurement may optionally be accomplished by a previously known device such as a Millar catheter 228 installed in left atrium 212 or left ventricle 216. The Millar catheter measures pressure (P) inside the chamber.

In an exemplary embodiment of the invention, system 200 monitors cardiac contractility indirectly, for example by detecting mechanical activation and/or electrical activation. Optionally, indirect measures of contractility are used to generate activation profiles. In an exemplary embodiment of the invention, an activation profile may be substituted for a contractility profile in determining whether changes in external intervention are desirable.

Optionally, a series of measurements are taken. In an exemplary embodiment of the invention, each measurement in the series is correlated to a specific time (t). In an exemplary embodiment of the invention, a series of pressure measurements correlated to time exhibit a cyclic repetition indicative of a cardiac cycle. This cyclically repeating function of pressure as a function of time is an example of a cardiac contractility profile. In an exemplary embodiment of the invention, pressure measurements are relative only to one another and no calibration in defined units is performed. Comparison may be, for example, to different cardiac cycles, different measurements within the same cycle, a running average, a previously established baseline or a pre-treatment value.

In an exemplary embodiment of the invention, dP/dt is calculated and evaluated. Measurements from catheter 228 are communicated to circuitry 230. Circuitry 230 may optionally be installed outside of body 240 or inside the body, for example adjacent to the heart. Circuitry 230 may contain analysis circuitry 232 and/or control circuitry 234 for a CCM electrode 235, mounted, for example on septum 220. In an exemplary embodiment of the invention, circuitry 230 implements a feedback loop on CCM electrode 235 in response to a detected imperfection in the cardiac contractility profile. Optionally, circuitry 230 determines when maximum dP/dt occurs and employs this data as a means of detecting an imperfection in the contractility profile. In an exemplary embodiment of the invention, the time of dP/dt (max) is correlated to contractility. Optionally, as contractility improves, dP/dt (max) occurs earlier.

For example, an electrical activation profile may indicate changes in timing and/or in morphology of electrograms. An ECG trace is a familiar example of an electrical activation profile. Electrical data may obtained intracardially, epicardially or from the periphery (e.g. on a surface of the body). For example, it is believed that the pre-ejection period (PEP) and/or changes in this parameter are useful indicators of cardiac contractility. In general, a PEP that falls within a known normal range (e.g. 96-120 milliseconds) is indicative of "healthy" contractility and a longer PEP is indicative of an "unhealthy" contractility.

In an exemplary embodiment of the invention, relative changes among various parameters are employed to construct an activation profile. In an exemplary embodiment of the invention, the activation profile is expressed as a plot of one or more variables as a function of time. In an exemplary embodiment of the invention, the activation profile is expressed as a relative timing between two or more events. For example, changes in timing, ratio or other relationship between two or more events may be used in constructing an activation profile. Optionally, one or more electrical events and one or more mechanical events are compared and/or analyzed as a group in order to generate an activation profile. Alternatively or additionally, data used in preparing an activation profile may be obtained from one or a plurality of locations. In an exemplary embodiment of the invention, one event used in preparing an activation profile is obtained from a local signal measured within the heart while data pertaining to one or more additional events is obtained from a distal measurement and/or measurement of a systemic parameter. In an exemplary embodiment of the invention, a profile is prepared by plotting data as a function of time.

A distal measurement is one taken at a distance from the heart. A systemic parameter is one which exhibits little variation regardless of the exact site at which it is measured. Parameters such as pulse rate, body temperature and blood oxygen saturation, although they may be subject to slight local variation. Measurement of systemic parameters is often conducted distally with respect to the heart. However, not all distal measurements are of systemic parameters.

In an exemplary embodiment of the invention, impedance measurements are used to detect changes in the mechanical activation of the heart, for example, between an electrode 222 in/on ventricular septum 220 and flowing to leads 224 and/or 226 in left atrium 212, or flowing to a casing containing circuitry 230. Alternatively or additionally, impedance measurements between one or more leads 224 and/or 226 positioned outside the body may be used to prepare a mechanical activation profile.

In an exemplary embodiment of the invention, acoustic measurements are used to detect changes in the mechanical activation of the heart. Cardiac acoustic data (e.g., sounds) may be measured, for example, by use of an acoustic sensor 236 located in the heart, for example on septum 220 and/or an acoustic sensor 242 located at some distance from the heart, for example on an outer surface of body 240 or in the casing of circuitry 230. Acoustic sensors include, but are not limited to microphones, stethoscopes and seismographs.

In an exemplary embodiment of the invention, acceleration measurements are used to detect changes in the mechanical activation of the heart. Acceleration data may be measured, for example, by use of an acceleration sensor 236 located in the heart, for example in septum 220. Accelerometers are commercially available and one of ordinary skill in the art will be able to choose an appropriate accelerometer and adapt it for use in the context of the present invention. One example of a commercially available accelerometer suited for use in the context of the present invention is a Biomechanical Endocardial Sorin Transducer (BEST) available from Sorin Biomedica (Saluggia, Italy).

In an exemplary embodiment of the invention, an accelerometer may be configured as a seismograph. Seismographs are commercially available and one of ordinary skill in the art will be capable of selecting a seismograph and integrating it into the present invention. For example, a cardioseismometer device produced by SEISMED (Seismed Instruments Inc., 13700 First Avenue North, Minneapolis, Minn. 55441) is suited for use in conjunction with the invention. Seismed described their seismograph measuring systems in the following patents: U.S. Pat. No. 4,989,611; EP 0 357 275 A1; U.S. Pat. No. 5,159,932; and U.S. Pat. No. D338,272. The specifications of all of these patents are incorporated herein by reference. The seismograph includes a detector (e.g. accelerometer) placed on the chest of a subject at the lower portion of the sternum. Changes in heart volume produce pressure waves in the chest. A weight on the detector (e.g. 1-2 Kg) facilitates measurement of changes in pressure, as opposed to sound. The pressure moves the weight and the resultant motion is measured by the accelerometer. Optionally, amplifiers and sampling equipment are used to record the signal onto a computer.

In some embodiments, a parallel synchronous ECG signal is captured and analysis software determines characteristic points in the signal. In an exemplary embodiment of the invention, time between events is determined. This method may be used to, for example, to determine raw and/or heart-rate adjusted total systole, Pre-ejection period (PEP), LV ejection time, PEP/LVET, total diastole; and isovolumetric relaxation time.

Figure 10:
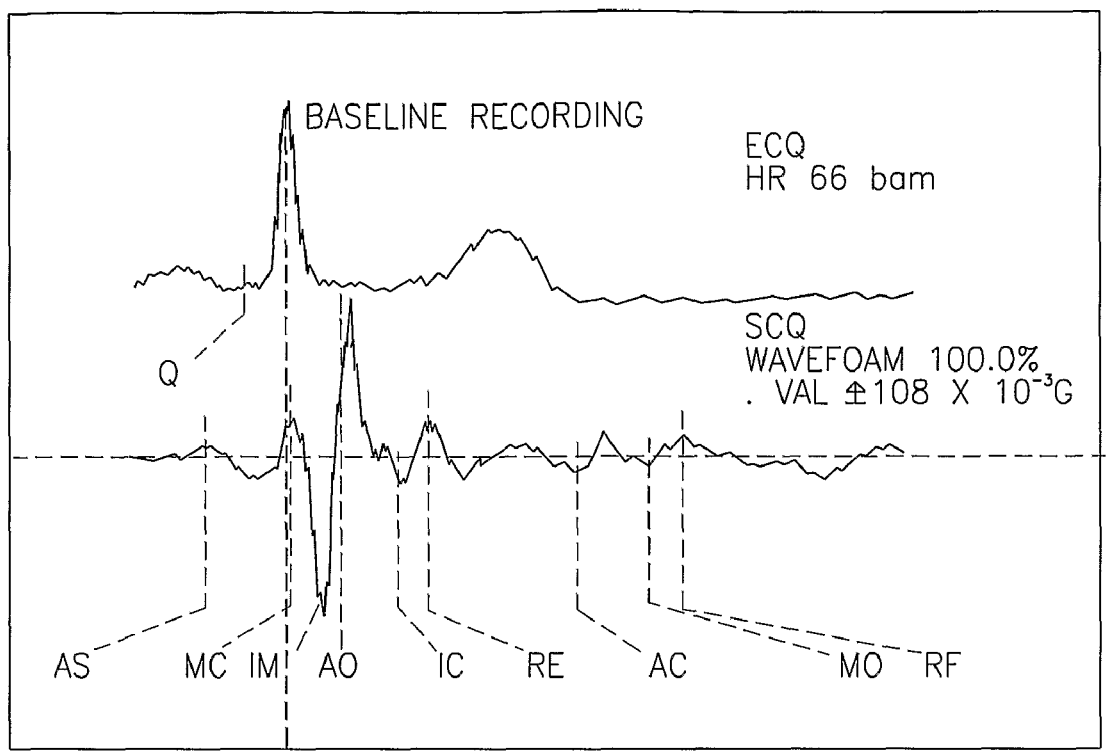
FIG. 10 is a graph illustrating cardiac seismography data as a function of time according to an exemplary embodiment of the present invention, aligned with an ECG trace.
Figure 10:
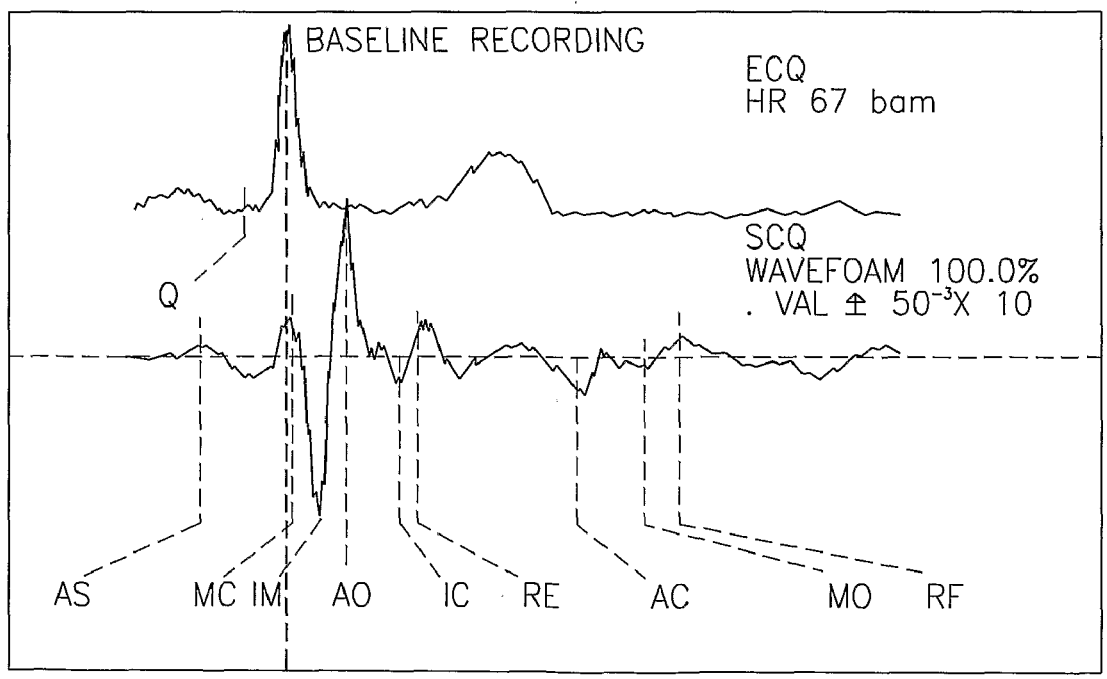

An exemplary output of a seismograph with a synchronized ECG trace is presented in FIG. 10 as an illustration of the utility of this exemplary embodiment of the invention. In FIG. 10, AS indicates atrial systole; MC indicates mitral valve closure; IM indicates isovolumetric movement; AO indicates aortic valve opening; IC indicates isotonic contraction; RE indicates rapid ventricular ejection; AC indicates aortic valve closure; MO indicates mitral valve opening; and RF indicates rapid ventricular filling;

On the ECG waveform of FIG. 10: R is at the same time as IM on the SCG; S is at the same time as AO on the SCG; and T is the wide wave that rise between RE and AC As in other exemplary systems 200, the acoustic system employs a series of measurements to create an acoustic profile in which acoustic data are presented with respect to time. Optionally, the measured signal amplitude is expressed as a function of time.

Exemplary protocols for the actual delivery of CCM signals to the heart and/or implantation of wires to deliver CCM signals is set forth in PCT publication No. WO 97/25098 and in U.S. Pat. No. 6,317,631, which are both incorporated herein by reference in their entirety. Following is a list of patents and publications which describe apparatus and methods which may be useful in conjunction with the present invention, the disclosures of all of which are incorporated herein by reference, as are the disclosures of all publications mentioned in this application:

Cardiac output enhanced pacemaker U.S. Pat. No. 6,463, 324, Apparatus And Method For Controlling The Contractility Of Muscles, U.S. Pat. No. 6,233,484, Controlling Heart Performance Using A Non-Excitatory Electric Field, U.S. Pat. No. 6,317,631, Muscle Contraction Assist Device, U.S. Pat. No. 6,285,906, Modulation Of Intracellular Calcium Concentration Using Non-Excitatory Electrical Signals Applied To The Tissue, PCT WO 01/24871 and PCT WO 00/12525, Electrical Muscle Controller, U.S. Pat. No. 6,363, 279, Electrical Muscle Controller using a Non-Excitatory Field, U.S. Pat. No. 6,330,476, Cardiac Output Controller, U.S. Pat. No. 6,298,268, Cardiac Output Enhanced Pacemaker, U.S. Pat. No. 6,463,324, Sensor Based Regulation of Excitable Tissue Control of the Heart, WO 00/27475, Regulation of Excitable Tissue Control of the Heart based on Physiological Input, WO 00/27476, Trigger Based Regulation of Excitable Tissue Control of the Heart, U.S. Pat. No. 6,587,721, Pacing with Hemodynamic Enhancement, PCT WO 00/04947, Delivery via RV Septum, PCT WO 01/82771A3, Anti-Arrhythmia Device having Cardiac Contractility Modulation Capabilities, PCT WO 01/30445, and Anti-Arrhythmic Device & a Method for Delivering Anti-Arrhythmic Cardiac Therapy, PCT WO 01/30139.

Exemplary Measured Physiological Parameters

In an exemplary embodiment of the invention, mechanical activation of the heart is determined based on changes in one or more of heart/chamber volume, valve opening/closing, blood flow, wall thickness, wall stiffness, and/or spatial displacement, velocity and/or acceleration of cardiac portions. These cardiac mechanical parameters may be measured in various ways.

As noted above, changes in contractility are expected to change the mechanical activation, which when measured, can indicate an effect of CCM.

In an exemplary embodiment of the invention, one or more of the following physiological parameters and/or measuring techniques is used to assess heart function: contractility, contractility changes, ejection fraction (EF), cardiac output (CO), stroke volume, relaxation, end systolic volume, end diastolic volume and estimated changes in systolic, diastolic vascular pressures, TDI (Tissue Doppler Imaging) as measured by ultrasound and oxygen consumption and/or oxygen saturation. These methods are known in the art and one of ordinary skill will be able to incorporate them into the context of the present invention.

In an exemplary embodiment of the invention, the effect of a therapeutic input, optionally a CCM delivery is evaluated. Optionally, the therapeutic input is deemed to have a positive effect if it concentrates cardiac activity in the early temporal phase of the heartbeat. A physician, based upon review of an activation profile generated according to the present invention, will be able to decide if the applied therapeutic input is appropriate with respect to one or more of amplitude, duration and timing by experimenting with amplitude and/or duration and/or timing and observed an effect on cardiac activity. Alternatively or additionally, the physician may decide whether the electrode is appropriately positioned. In an exemplary embodiment of the invention, this type of analysis may be applied to individual electrodes within a group of two or more electrodes.

In an exemplary embodiment of the invention, biochemical indicators of a change in cardiac function are employed. Biochemical indicators may include, but are not limited to phosphorylation of specific proteins as taught in co-pending U.S. patent application 60/677,761 and PCT/US04/07589, the disclosures of which are fully incorporated herein by reference. Alternatively or additionally, biochemical indicators may include substrate concentrations in the blood, such as oxygen and/or carbon dioxide concentrations. In an exemplary embodiment of the invention, local biochemical changes assayed at the level of protein activity and/or gene expression and/or mRNA stability and/or DNA phosphorylation and/or electrical or mechanical activity. Optionally, biochemical measurements are conducted close to the CCM electrode(s). Moreover, changes due to electrode polarization should be overcome.

In an exemplary embodiment of the invention, physical measurements from outside the heart are employed to indicate cardiac function. For example, pressure and/or volume in coronary arteries, coronary sinuses, or peripheral blood vessels may be employed as indicators of contractility and/or contraction timing. These parameters may be measured over time and used to prepare activation profiles.

In an exemplary embodiment of the invention, elongation and/or shortening and/or morphology change of an action potential profile is indicative of cardiac contractility. Alternatively or additionally, analysis of temporal coordination, or lack thereof, among action potential profiles is employed in making a diagnosis. In an exemplary embodiment of the invention, evaluation of the repolarization phase locally and/or globally is employed to measure synchrony and/or stability. In an exemplary embodiment of the invention, T-Wave alternance measured at the body surface is employed as to assess changes in cardiac performance, for example by possible changes related to relaxation timing and/or related to cardiac contractility. In another exemplary embodiment, measurement may include timing of local cardiac activity, and it can be processed to evaluate relative timing among events and locations.

General Criteria for Suitable Measurement Parameters:

The scope of the invention includes a large variety of suitable measurement parameters which may be correlated to indicators of cardiac function, for example contractility. Optionally, the correlation to cardiac function (e.g. contractility) is initially made by correlating the indicator with an additional measurement parameter, such as LVP.

In an exemplary embodiment of the invention, a suitable parameter is a parameter which is not subject to CCM interference so that the CCM regimen does not create an artifact with respect to measurement of the suitable parameter. Peripheral blood pressure is an example of such a parameter.

In some exemplary embodiments of the invention, a low voltage CCM signal is employed to reduce artifacts to an acceptable amplitude. Alternatively or additionally, the CCM signal may be applied concurrently or sequentially through two or more leads as a means of reducing artifact amplitude.

Typically, the sensitivity and/or suitability of a measurement parameter as a measure of contractility is initially assessed by comparing and/or correlating to a previously used and established measure. For example, a temporal profile of local impedance between two leads might be temporally aligned to a contractility profile based upon directly measured ventricular pressure data. The alignment permits identification of at a characteristic feature in the impedance profile which correlates to dP/dt (max) in the contractility profile.

Once a correlation between a proposed new measurement parameter and an established measure has been made, the new measurement parameter may be deemed suitable and substituted for the established measure.

In an exemplary embodiment of the invention, once a new measurement parameter has been correlated to a known measurement parameter in some patients, subsequent patients may be evaluated using the new measurement parameter without correlation to the known measurement parameter.

Millar catheter measurements of LVP are conducted after femoral artery catheterization to place the catheter in the heart and the catheter itself costs hundreds of dollars. Identification of a new measurement parameter well correlated to LVP is significant both medically and financially.

Methods for measuring, impedance, acoustic data, motion (e.g. by a seismograph or accelerometer) and Left Ventricle Volume (LVV) as approximated by sonometry are described in greater detail hereinbelow.

In an exemplary embodiment of the invention, a suitable measurement parameter involves long term measurements. These long term measurements are not directly correlated to specific events within a single cardiac cycle. However, long term measurement permits discovery of changes, hopefully improvements, in cardiac function which may not be apparent in an acute measurement. Long term measurement permits analysis of parameters including, but not limited to, clinical signs and/or physiologic function.

Clinical signs include, but are not limited to global indicators of patient condition. Global indicators of patient condition include, for example, subjective evaluation of feeling and/or assessment of performance with respect to specific activities. Feeling may be assessed, for example, by evaluating appetite and/or eating habits and/or sleep patterns and/or sleep duration and/or breathing (apnea), orientation to surroundings or level of interest in specific topics. Performance may be assessed, for example, with respect to walking distance and/or rate of accelerations and/or daily living skills.

Physiologic function includes, monitoring of parameters such as oxygen saturation and/or weight and/or blood pressure (average systolic and diastolic pressure, as opposed to variations within a single heartbeat) and/or respiration rate and/or respiration volume.

In an exemplary embodiment of the invention, long term measurements are directly related to the heart. Optionally, long term measurements include measures of heart dimensions and/or heart rate variability and/or rate of arrhythmia and/or changes in these or related parameters.

Location Determination

In an exemplary embodiment of the invention, a lead is placed at what is believed to be a desirable location and the suitability of the location is tested. Testing is accomplished by delivering an electrical signal through the lead and observing the effect on one or more activation profiles using, for example, data parameters described hereinabove and hereinbelow. In an exemplary embodiment of the invention, analysis of the effect of the delivered electrical signal on the activation profile indicates that the lead is either on the ventricular septum or is in a less desirable location (e.g. RV free wall, tendons, valve, trebecular muscle or papillary muscle). In an exemplary embodiment of the invention, the lead is intended as a CCM electrode and a decision is made about whether to reposition the lead or leave it in place.

In an exemplary embodiment of the invention, a lead position is determined to be either on or off the HIS bundle according to the influence of a signal delivered through the lead. Influence of the signal may be, for example, on a morphology of the QRS wave pattern and/or on the time between signal delivery and dP/dt (max).

For example, if lead placement is correct, contraction should remain coordinated when a signal is delivered through the lead. If lead placement is incorrect, contraction may become disjointed or confused when the signal is delivered. Therefore, a parameter such as the QRS pattern of an ECG and/or time to dP/dt max and/or PEP and/or heart motion may be employed to assess lead placement.

For example, a significant widening of the QRS pattern in response to a pacing signal indicates that the lead is positioned in a location other than on the HIS bundle of the septum. Relocation of the lead may be considered in this case. In contrast, delivery of the pacing signal through a lead correctly placed on the HIS bundle of the septum produces no significant widening of the QRS pattern of the ECG. Normal variation of the QRS pattern from contraction to contraction may be in the range of 5 milliseconds. Widening of the QRS pattern in response to an applied signal of 10, optionally 20, optionally 30 milliseconds or more is significant and may be considered indicative of incorrect lead placement.

Alternatively the waveform pattern of the impedance and/or the MAP signals can indicate if the location of lead is good or if repositioning is needed. In an exemplary embodiment of the invention, if the lead is placed on the septum, the local sense (LS) is close to a global minima point of the heartbeat in the impedance channel. The MAP channel permits detection of LS which serves as a landmark location in the impedance channel and permits analysis of the waveform. Therefore, if the LS is far from the global minima of the heart beat, it indicates that the lead is not attached to the septum. If the impedance waveform is too complex, and includes multiple maxima and/or minima points for each heartbeat, determination of the global maxima and global minima may not be feasible. In this case repositioning of the lead should be considered.

Evaluation of CCM Signal

In an exemplary embodiment of the invention, once it has been determined that a lead is located in a correct position (e.g. on the HIS bundle) a CCM signal may be applied through the lead. Analysis of data pertaining to, for example, one or more of the parameters detailed hereinbelow can provide information about cardiac contractility in the presence of the CCM signal. Comparison to similar data collected before and/or after administration of the CCM signal may be used to evaluate the efficacy of the CCM signal variable (e.g. pulse amplitude and/or delay and/or duration).

In an exemplary embodiment of the invention, shortening of contraction time and/or occurrence of certain events earlier in the cardiac cycle is indicative of an acceptable CCM signal. Optionally, successively lower CCM input signal amplitudes are tested. In an exemplary embodiment of the invention, a lowest CCM input signal which provides the desired activation profile is chosen. Optionally, this extends battery life.

Invasiveness

Various embodiments of the invention utilize different measuring methods which have different degrees of invasiveness.

For example, sound measurements and accelerations of the chest can be measured from outside the body in a non invasive manner.

An intermediate degree of invasiveness occurs when sensors are integrated into existing invasive elements such as a CCM device. A CCM device may include, for example leads (e.g., impedance and/or acceleration leads) or casing (e.g., impedance and/or intra-chest pressure) which also function as sensors.

The greatest degree of invasiveness occurs when a sensor is implanted solely for measurement, such as a Millar catheter.

Temporal Analysis

It is a feature of some embodiments of the invention that the analysis focuses on changes in timing of various measurements, rather than on amplitude. For example, rather than determine the valve speed when it opens, what is determined is the opening time relative to the start of the cardiac cycle or other milestone in the cardiac cycle. Use of timing rather than amplitude allows for comparisons to be made over a long time period even if external sensors (when they are used) are removed between tests.

In an exemplary embodiment of the invention, measurements are provided with a time stamp. Optionally, the activation of the heart is known from electrical measurements (e.g., ECG). In an exemplary embodiment of the invention, measurements are normalized and/or binned according to heart rate and the time stamp is a time stamp relative to the cardiac cycle.

In an exemplary embodiment of the invention, a baseline signal for a cardiac cycle is provided, for example, as a template (e.g., how the impedance measuring changes, in general, as a function of proportionate time in the cardiac cycle.) In an exemplary embodiment of the invention, the start of a cardiac cycle is detected from the measured signal, by comparing to the template. Alternatively or additionally, certain features are searched for, for example, a sudden peak followed by a time of no change may indicate end-diastole.

In an exemplary embodiment of the invention, the baseline signal is LVP collected for seconds to tens of seconds. A minimal and a maximal level LVP are estimated. An arbitrary threshold is set, for example 30% of the swing from minimum to maximum in the increasing phase of the pressure cycle. This arbitrary threshold defines a division between two heart beats. The definitions of minimum and maximum and the threshold may include robust estimators to avoid artifacts from arrhythmia or other sudden events. For example, the 5-10% extreme values may be ignored (such that min is defined as the 5% lowest 5% value, and max as the 95% highest value). In an exemplary embodiment of the invention, the threshold is set to the median LVP value.

Once a demarcation between two beats has been identified, the calculation of the slope and identification of dP/dt (max) serves to indicate the timing of contraction within the beat. Smoothing of the signal in the vicinity of the detected dP/dt (max) may be performed, for example by band-pass-filter, or Savitzky-Golay filter. In an exemplary embodiment of the invention, dP/dt is calculated for time increments of 10 milliseconds or less.

In an exemplary embodiment of the invention, the baseline and/or experimental heart beat pattern is averaged over several beats after synchronization. Synchronization may be, for example by local sense or QRS or any other desired feature. In an exemplary embodiment of the invention, averaging improves signal quality and accuracy. Optionally, averaging reduces the effect of unrelated physiologic and/or environmental parameters.

In an exemplary embodiment of the invention, averaging or template matching is conducted on data from multiple heartbeats to reduce an effect of aberrant heartbeats. Optionally, data is collected over 10, optionally 20, optionally 30, optionally 50 optionally 100 heartbeats or greater or lesser or intermediate values. In an exemplary embodiment of the invention, aberrant beats are detected and excluded. Optionally, aberrant beats refers to arrythmias.

In an exemplary embodiment of the invention, analysis includes identification of salient features in the data, for example, peaks, valleys, plateaus, double peaks, maximum derivative, minimum derivative, moments matching, template matching and principle components analysis (PCA).

In an exemplary embodiment of the invention, analysis comprises identifying changes in order and/or relative delays between such features. Such changes generally indicate changes in the mechanical activation of the heart. Typically, but not always, a shortening of delays indicates a more contractile heart. Optionally, shortening of delay by 20 milliseconds or more, optionally 30 milliseconds or more, optionally 40 milliseconds or more indicates an improvement in contractility. Alternatively or additionally, detection of a % change of a short phenomenon, like pre-ejection period (PEP), and/or detection of % changes in time scales like R-R intervals may be indicative of improved contractility. Optionally, a 5% change, optionally a 10% change or more change is indicative of improvement.

In an exemplary embodiment of the invention, profiles from multiple beats are combined, for example, by regular averaging or by matching up the signals before combining.

Artifact Reduction

Typically, but not always, the CCM signal is applied at times which include measurements of interest. However, the CCM signal is typically of a magnitude which interferes with measurement.

In an exemplary embodiment of the invention, the measurement is made in a manner which avoids CCM interference. Avoidance of CCM interference may be achieved, for example by shutting off the measuring system during application of the CCM signal. Optionally, shut-off is achieved by having the CCM circuitry provide a timing signal to the measuring circuitry. Optionally, the two circuitries are in a same casing and/or share a controller. Alternatively or additionally, the timing of the CCM signal as a function of cardiac cycle is detected by the measuring circuitry which responds by anticipating CCM signal duration and/or timing and shutting down at appropriate times. Alternatively or additionally, parameters of the CCM circuitry, for example, delay and duration are provided to the measuring circuitry.

In some embodiments of the invention, the effect of a CCM signal lasts more than one heart cycle and CCM is not applied during a heart cycle used for measurement. Optionally, some types of measurements are made every cycle and other types of measurements are made only when CCM is not applied.

In an exemplary embodiment of the invention, measurement continues during the CCM signal and artifacts resulting from the CCM signal are blanked out, for example by the measurement or analysis circuitry. Optionally, the duration of the CCM interference is determined for each patient.

In an exemplary embodiment of the invention, CCM artifacts are reduced by measuring at a distance from the CCM input delivery site. In an exemplary embodiment of the invention, one lead delivers CCM while another makes an intracardiac measurement at another location. If CCM is to be delivered in each heart beat, this approach may be alternated, such that on one heart beat lead A delivers CCM and lead B is used for measurements, while in another heart beat lead B delivers CCM while lead A is used for measurements.

In an exemplary embodiment of the invention, CCM inputs are reduced, but not shut off, while measurements are being conducted. Optionally, the CCM input remains effective even after a reduction in amplitude.

In an exemplary embodiment of the invention, data processing is undertaken to replace the artifactual data which has been blanked out. In one example, if a peak is blanked out, the rate of the peak rise is estimated from the rate of decay. In another example, if a peak is blanked out, the rate of the peak decay is estimated from the rate of rise. Alternatively, both rise and decay serve to estimate peak location and magnitude, for example by a polynomial fit, or other parametric interpolation or extrapolation algorithm. In another example, timing is compared to the relaxation time of an event, rather than to the initiation of the event. In another example, later maxima and minima events, their magnitude and/or timing or other relations between them serve as alternative measures, or serve to estimate the desired peak. In another example, missing data is interpolated, for example from data in the same cardiac cycle or data form cycles without CCM.

In an exemplary embodiment of the invention, interpolation algorithms are implemented to supply missing data resulting from elimination of CCM artifacts. Optionally, bi-linear and/or bicubic interpolation algorithms are suitable for use in this context. Alternatively or additionally, a polynomial fit with data outside the CCM artifact period is employed to generate missing data. For example, polynomials in the orders of 2-6 may be suitable for such analysis. Alternatively, a sinusoidal or other harmonic function may be used for fitting the measured data outside the CCM artifact.

Uses of Measurement

In an exemplary embodiment of the invention, measurement of CCM effect is carried out before CCM device implantation. For example, as part of an assessment of suitability for a patient, temporary CCM electrodes (or external electrodes) are used to control the heart. Measurement of contractility changes are then optionally used to decide if CCM is a suitable treatment or to select between multiple devices and/or treatment parameters.

In an exemplary embodiment of the invention, assessment is carried out during implantation. Optionally, the assessment considers whether or not a device to be implanted is carrying out its function, or what optimal parameters are. Optionally, it is noted that implantation is generally not an exact science. Thus, a device may fail to work even if pre-testing indicated it would have a beneficial effect. Optionally, contractility change assessment is used to fine tune device settings to compensate for imperfect implantation.

In an exemplary embodiment of the invention, assessment is carried out after implantation, for example, to detect long term improvements caused by CCM or to detect short term improvements (e.g., acute effect of a CCM signal). Optionally, assessment is used as part of large group studies, for example, to assess statistical efficacy of a certain CCM regime. The device optionally transmits contractility assessment results to an external controller, for example, using wireless methods and/or using a data line to a centralized location.

In an exemplary embodiment of the invention, a search of CCM signal parameters is used to optimize signal parameters, with contractility assessment as described herein being used as feedback for the search process.

A wide range of measurement methods and apparatus are described herein. It should be noted that different methods may be more suitable for different situations.

For example, ongoing monitoring of contractility may benefit from a small device that is either implanted (optionally as part of a therapeutic device which is to be implanted in any case) or is unobtrusive, even if precision suffers.

In another example, during implantation surgery, minimization of tubes placed into the body may be desirable. For this reason an external device, even a large non-portable device, may be preferred in a surgical context.

In another example, initial experimentation and/or calibration employs an implantable device (e.g. a Millar catheter) and a non-implanted device (e.g. seismograph or acoustic monitor) is used for subsequent monitoring. Optionally, subsequent monitoring is only periodic monitoring, for example monitoring performed during clinic visits. For monitoring performed during clinic visits, there is no incentive to design a portable device and emphasis may be place on accuracy.

In another example, during implantation of a device for CCM, impedance measurements are conducted using leads placed on the heart. The impedance measurements are used to verify correct placement and/or adjust operational parameters. In an exemplary embodiment of the invention, the impedance leads are removed at the end of surgery. Optionally the impedance leads can remain implanted. Optionally, impedance measurement can be integrated into the same leads delivering the CCM therapy. Optionally, the impedance is measures from the same electrodes within the leads, which are used to deliver CCM signals. Optionally, post operative patient monitoring may be based upon acoustic data, for example acoustic data acquired with a stethoscope.

According to various exemplary embodiments of the invention pacing leads and/or defibrillation leads and/or multiple electrode leads are employed. In an exemplary embodiment the lead may have two electrodes, used for sensing tissue electrical activity, CCM signal delivery, and impedance measurements. In an exemplary embodiment of the invention, a pacing lead such as St. Jude 1388T is employed.

While the above description has focused on CCM signals, cardiac function assessment (e.g. contractility assessment) may be used in conjunction with other treatments. In one example, some pacing sequences (e.g. Re-Synchronization therapy and/or B-Ventricular pacing) and some drugs are supposed to improve contractility. The methods/apparatus described herein can be combined with a pacemaker, or be in an externally worn vest, to provide feedback for such therapy.

In an exemplary embodiment of the invention, leads of an implantable device according to the invention produce chronic contractility information along the course of treatment of cardiac resynchronization.

While the above has focused on positive effects, such as increase in contractility, also negative effects, such as decrease in contractility can be detected. Detecting decreased contractility may be useful, for example, in monitoring progress of a degenerative condition. In an exemplary embodiment of the invention, an internal monitor supplies data to a controller which periodically adjusts CCM delivery to compensate for degeneration. According to various embodiments of the invention, direct or indirect measures of contractility can be employed. Indirect measures of contractility include, but are not limited to, electrical parameters (e.g. impedance), flow parameters (e.g. ejection fraction) and acoustic parameters (e.g. PCG or portion thereof).

In an exemplary embodiment of the invention, the assessment methods described herein are used for assessing other cardiac functions, in addition to or instead of contractility. In one example, changes in valve timing are used to assess improvement in inter-ventricle activation delay.

Details of Exemplary Measuring Methods

A particular property of various methods of measurement described herein is that calibration of the sensor to absolute value is not required. Rather, in some embodiments of the invention, what is measured is a change in contractility and its correlation to CCM treatment. Optionally, however, a basic matching of the measurement to mechanical activation is provided. For example, if what is measured is impedance of the heart as a whole, a step of correlating this measurement with contractility is optionally carried out. Optionally, however, this correlation step is carried out in a manner which is not patient specific, for example for a device and/or set of electrode locations. Optionally, a testing is made for a particular patient to see if the "known" correlation is correct for that patient too. For example, a change in mechanical activation may be artificially induced, for example, by exercise and detection of an associated change in contractility detected using the methods described herein. If an expected change in contractility is detected, then the correctness of correlation for that patient is optionally assumed. Optionally, the method used for correlation in some embodiments of the invention is less sensitive to noise as it uses changes in timing to detect changes in contractility, so that changes can be detected even if their actual amplitude is unclear.

Optionally, a validation process of comparing sensed signals to contractility is carried out in patients where the location of electrodes (or other sensors) may not be optimal.

Optionally, validation and/or calibration is carried out by comparing the signal to a non-contractility signal, for example, to ejection fraction or another signal with a higher confidence of being indicative of contractility changes.

Direct Measure of Contractility

In some embodiment of the invention, contractility is directly measured, for example, using a Millar catheter. However, such direct measure is preferably avoided, when indirect measures are available.

Direct Measure of Mechanical Activation Profile

In an exemplary embodiment of the invention, the mechanical activation profile of the heart is directly measured and this is used as a correlate of changes in contractility.

In an exemplary embodiment of the invention, optical or acoustic imaging techniques are used as known in the art.

In an exemplary embodiment of the invention, the motion and thickness changes of multiple parts of the heart are detected, for example, using local acoustic or impedance images and/or position or acceleration sensors. An exemplary method is described in U.S. Pat. Nos. 5,738,096; 6,066,094 and 6,285,898 the disclosures of which are incorporated herein by reference. Optionally, sensors are attached to tissue where changes in motion are expected and/or easy to measure, for example, valve openings and closing.

Measure of a Direct Effect of Mechanical Activation Profile or Contractility Change In an exemplary embodiment of the invention, a direct effect of the activation is measured, for example, a non-ventricular pressure profile measured using a Millar catheter.

Alternatively or additionally, a direct effect of increase in contractility is measured, for example, ejection fraction.

In an exemplary embodiment of the invention pressure is measured at a location and/or quality which is sufficient to extract a dP/dt signal. For example, pressure may be measured in the aorta and/or an atria and/or a peripheral artery. Optionally, the pressure is measured outside of the vascular system, for example, in the chest, optionally near the heart. In an exemplary embodiment of the invention, peripheral blood pressure is used as an indicator of contractility.

Measure of Indirect Effect

In an exemplary embodiment of the invention, measurement is made of a composite parameter which is only generally associated with activation profile and/or contractility change. However, it is expected that even for a parameter only generally associated, changes in the timing of mechanical activation in different parts of the heart will affect this parameter in a qualitative manner which is detectable and able to be used as an indication of change in contractility (even if the magnitude of change may not be available).

In an exemplary embodiment of the invention, the indirect effect that is qualitatively detected is the timing of gross events in the heart, for example, heart motion, changes in volume or impedance and/or sounds. Optionally, the first derivative of a parameter with respect to time is calculated and a maximum in the first derivative is used as an indicator. In an exemplary embodiment of the invention, the time to reach a maximum value of the first derivative is employed as an indicator.

According to various embodiments of the invention, any parameter or combination of measured parameters may be employed in preparing an activation profile, as long as it may be sufficiently correlated to changes in the myocardium to have predictive value. Parameters which are sensitive enough to register the equivalent of dP/dt (max) change of above ~5% may be considered predictive and can be employed as decision tools.

Impedance

In an exemplary embodiment of the invention, impedance measurements of gross-portions (or all) of the heart are used to indicate changes in gross-shape and/or function of the heart. These changes generally correlate with mechanical activation. In one example, it is expected that impedance change between a lead and a casing will change when an intervening heart part empties and/or fills with blood and/or thickness of muscle changes. Alternatively or additionally, gross motion of a lead can be detected based on changes of impedance between the lead and a casing.

Various configurations for impedance measuring electrodes may be used, for example, between the stimulation lead and the casing, on opposite sides of the left ventricle, at base and apex of heart, between two veins, on either side of a valve, two electrodes in the ventricle, one lead outside the body and one lead inside the body and two leads outside the body.

Measurement between electrodes may be between those portions located in the blood (e.g. ring to ring) or between those portions embedded in the tissue (e.g. tip to tip) or combinations (tip to ring). Alternatively or additionally, tip to ring impedance of a single electrode may be measured.

In exemplary embodiments of the invention, more than two electrodes employed and measurements of multiple pairs selected are conducted concurrently. For example, electrodes A and B which are on both sides of the chest, and electrodes C and D which are in the ventricle may be employed. This arrangement permits measuring impedance between A-B; A-C; C-B; A-D; D-B and C-D. Impedance data from each pair of electrodes may be collected and analyzed separately, comparatively or in full or partial aggregation.

In an exemplary embodiment of the invention, combining data from two or more electrodes in the same vicinity permits generation of a 'virtual electrode', which effectively represents a signal from a location which is in the vicinity of the group of electrodes, but not in the exact position of any one of them. Optionally, the electrodes may be dedicated electrodes or they may be shared with the stimulation system and/or other sensors (e.g., ECG sensors).

As noted above, in an exemplary embodiment of the invention, impedance measurements are optionally not carried out during CCM application even if separate electrodes are used for impedance and for CCM. In an exemplary embodiment of the invention, CCM leads are employed for impedance measurements. Optionally, a single lead is not simultaneously employed for CCM signaling and impedance measurement. In an exemplary embodiment of the invention, impedance measurement electrodes are separate from CCM electrodes. In an exemplary embodiment of the invention, an electrode is employed both for CCM and for impedance measurement. Optionally, each electrode in a plurality of electrodes is employed for both CCM and impedance measurement, but no single electrode is employed simultaneously for both purposes.

Figure 11A:
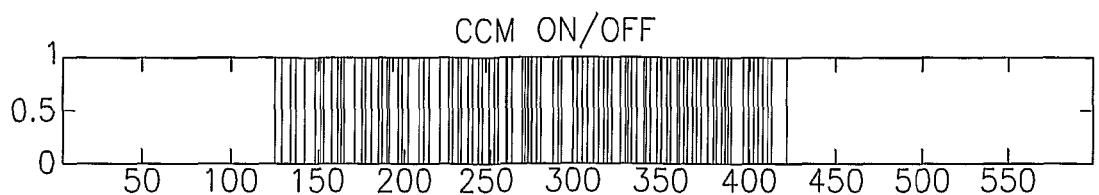
FIGS. 11A; 11B; 11C 11D and 11E are plots of CCM signal, max dP/dt, LS_maxZ1, LS_maxZ2 and LS_maxZ12 respectively.
Figure 11B:
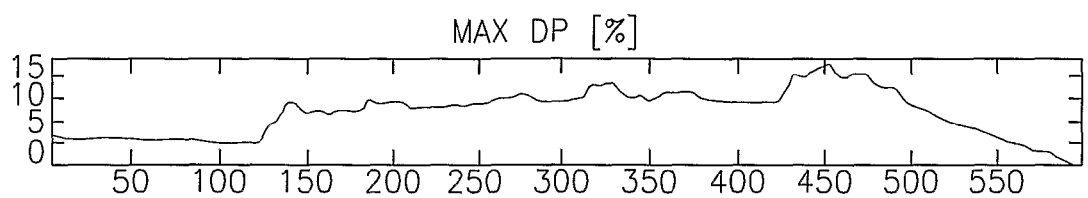
Figure 11C:
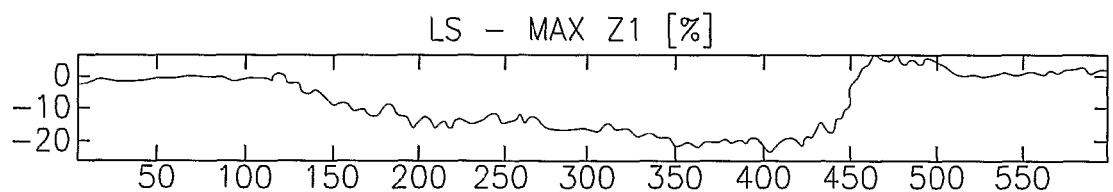
Figure 11D:
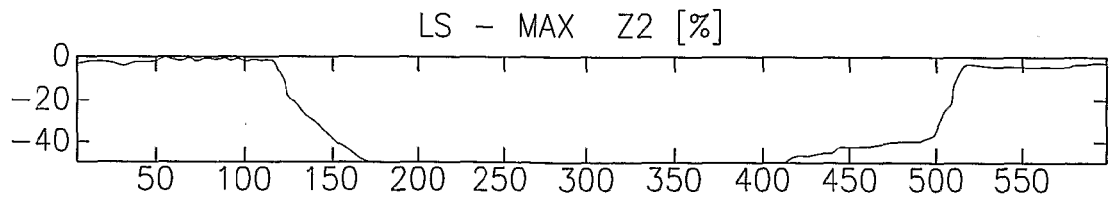
Figure 11E:
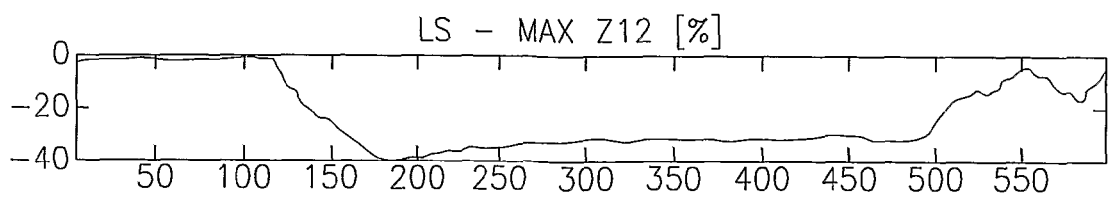

FIGS. 11A-11E present data from an experiment conducted in a pig using two leads (lead 1 and lead 2; each lead having a tip and a ring). FIG. 11A labeled "CCM on/OFF" consists of zeros (white) when there are beats with no CCM signal and ones (shaded) when there are beats with a CCM signal. FIG. 11B labeled "max dP/dt" shows the maximum change in pressure per unit time for each heart beat. FIG. 11C labeled "LS_maxZ1: indicates the time from LS (local sense) to maxZ1 (First maxima after LS in impedance channel1 which measure impedance in lead1 between tip1 to Ring1) for each beat. FIG. 11D labeled "LS_maxZ2" indicates time from LS (local sense) to maxZ2 (First maxima after LS in impedance channel2 which measure impedance in lead2 between tip2 to Ring2) for each beat. FIG. 11E labeled "LS_maxZ12" indicates: time from LS (local sense) to maxZ12 (First maxima after LS in impedance which measure impedance in lead2 between tip1 to tip2) for each beat.

The values in plots 11B, 11B, 11C, 11D and 11E indicate percentage of change relative to a baseline value. The baseline value is an average of one minute before CCM started.

These graphs illustrate that as max dP/dt rises, the time between local sense and the following max impedance point becomes shorter. Therefore, these data are indicative of cardiac contractility.

Acoustics

While local acoustic sensing may be used to assess tissue stiffness and/or mechanical activation and acoustics may also be used for imaging, in an exemplary embodiment of the invention, sounds generated by the heart and/or blood flow therein are used as indicators of contractility and/or cardiac function.

In an exemplary embodiment of the invention, changes in Doppler signals from the heart and/or blood are correlated with the cardiac cycle. Alternatively or additionally, sounds generated by valves opening and/or closing and/or speed of blood flow and/or turbulence are correlated with the cardiac cycle.

In an exemplary embodiment of the invention, a sound pick-up is provided inside the body or outside the body. The sound pick up may include, for example a stethoscope and/or a microphone. Optionally, the pickup includes an interface to analytic circuitry. In an exemplary embodiment of the invention, the analytic circuitry translates the signal pattern into events associated with the cardiac cycle such as valve movement and/or blood flow from chamber to chamber.

Acceleration

In an exemplary embodiment of the invention, acceleration of a portion of the heart is used as a correlate with contractility changes. In an exemplary embodiment of the invention, acceleration is measured using an intra-cardiac lead that includes an accelerometer, for example, Biomechanical Endocardial Sorin Transducer (BEST; Sorin Biomedica, Saluggia, Italy Alternatively or additionally, acceleration of the chest is measured, for example, using an external accelerometer. Alternatively or additionally, the accelerometer is inside the chest, but outside of the heart, for example, in a pacemaker casing. Optionally, the accelerometer is inside the rib cage.

It should be noted that acceleration of a part of the heart or the heart as a whole may not be indicative of the exact activity of the heart segment (or center of gravity) being measured. For example, the actual acceleration may depend on one or more of acceleration of nearby tissue, movement of blood and contracting and expanding of other heart chambers. However, it is expected that the pattern of acceleration and/or acceleration changes be correlated with the cardiac mechanical activation as well as overall motion of the heart during a heartbeat.

In an exemplary embodiment of the invention, noise in the form of whole body acceleration and/or vehicle acceleration are corrected for by providing two accelerometers, one more closely coupled to the heart (or vascular tissue) than the other, for example, one accelerometer in a casing and one in the heart.

Following is a brief description of a setup and signal processing method that correlates contractility (dP/dt) with acceleration.

A patient is placed on an operating table. CCM leads are connected to the ventricular septum, in the right ventricle. A timing lead (to measure ECG) is optionally provided in the right atrium. A Sorin accelerometer lead is attached to the septum and used only to measure acceleration (e.g., using the pacemaker electronics only for measuring and not for pacing).

A Millar catheter is placed in the left ventricle. A pressure profile based on data collected by the catheter is compared to a profile of acceleration (or speed or displacement) of the septum as a function of time.

Processing of the Millar signal is as follows: in the received pressure signal, beats are identified (optionally using timing catheter) and the maximum slope (dP/dt) is identified. Sampling rate is 1 ms and the signal is optionally smoothed to reduce noise, for example, using a Savizky-Golay filter, which maintains derivatives. This signal is optionally averaged over several beats, for example, 30 beats. Optionally, outliers are dropped. Optionally, the signals are binned and/or normalized according to heart rate. It is noted that CCM sometimes lowers heart rate.

The resulting value may be used as a contractility value. This value is then optionally used as a baseline to assess the effect of CCM and/or sensitivity of acceleration based detection.

A similar processing may be used for acceleration measurement. Maximum contractility is optionally indicated by maximum acceleration. Displacement and/or velocity are optionally determined by integration. As with pressure signals, signals from different heart beats may be combined before or after processing, for example, by matching up of features and/or normalizing according to heart rate and/or arrhythmia states/modes.

In an exemplary embodiment of the invention, blanking is applied during CCM application. Missing data is, for example, ignored or interpolated. Optionally, only good data points are used, for example, using only relaxation time (minimum, maximum, average) and not rise time. Optionally, one (e.g., relaxation time) is used to estimate the other (e.g., rise time). Optionally, what is measured is delay between electrical activation (e.g., of the heart or chamber) and mechanical activity. Change in such a delay can be determined from the relaxation time as well as from the rise time. In some cases, as contractility goes up, delays get shorter The contractility affecting circuitry and contractility estimating circuitry may be provided in a single device or in multiple devices, optionally synchronized devices.

While a Millar catheter is described, optionally, only the acceleration sensor is used and the Millar catheter is used only to validate the general correlation between acceleration and pressure.

It should be noted that as in other measured parameters, the acceleration measurements may repeat (or appear to repeat) over a single cardiac cycle. Optionally, a separate input is used to indicate the start of the cardiac cycle (or other landmark). For example, an ECG sensor or a pacing source may provide a separate input. The separate input is correlated to time to permit registration with acceleration data (or any other measurement parameter). Registration of a landmark of the cardiac cycle on the acceleration data permits identification of which one of the two peaks of acceleration relates to contractility (if there is a particular one). Similarly, if the delay between two such acceleration peaks is of interest, the selection of peaks can be aided by knowing when the cycle starts. It is expected that contractility modulation (e.g. CCM) will produce small changes in the overall time-line of mechanical activation and/or sensed signal. These small changes are typically expressed as a change in timing between events, optionally a delay of a second event with respect to a first event. In some cases, the order of events may be changed by contractility modulation. Optionally, such changes are detected during a per-patient, per disease and/or per-measure validation.

Hemodynamic Measurements

Other physiological measurements may have a general correlation with contractility. For example, various vascular measurements may be indicative. In one example, arterial pressure is used as a measure, for example using an inflow pressure catheter. In another example, flow rate or flow volume (e.g., using a portable acoustic imager) are used. In another example, a Swan-Gantz catheter is used. In another example, arterial wall motion is used. In another example, plethysmography is used.

Electrical Signals

In an exemplary embodiment of the invention, electrical signals are used instead of or in addition to mechanical activation signals to assess changes in cardiac function. Optionally, assessment is via a correlation to contractility. The correlation may be either direct or indirect.

In one example, the activation profile, for example shape of ECG or change in ECG vector over time, is used. In an exemplary embodiment of the invention, a series of ECG signals for different contractility conditions are collected from the patient in question in conjunction with contractility measurements and used for assessment.

In an exemplary embodiment of the invention, T-wave alternance is used as an indicator of cardiac function. Optionally, a change in alternance is used to indicate an increase in contractility. Optionally, the change is a reduction. In an exemplary embodiment of the invention, T wave alternance is measured in the presence and absence of an input signal, such as a CCM signal, as a means of evaluating the effect of the signal.

Optionally, the above detection of contractility using mechanical activation sensing measures changes in variance of electrical activity as opposed to changes in mechanical activity. Depending on the situation, increased or reduced variance may indicate increased or reduced contractility.

Ventricular Volume

In an exemplary embodiment of the invention, Left Ventricle volume LVV is presented as a function of time so that a volume profile is formed. Optionally, LVV is approximated by Sonometry. In an exemplary embodiment of the invention, dLVV/dt is analyzed and dLVV/dt (max) is used as an indicator of maximum contraction.

Additional Relevant Parameters

In an exemplary embodiment of the invention, synchrony of mechanical and/or electrical events from beat to beat is used as an evaluation parameter. Optionally, this includes evaluation of heart rate variability, rate of arrhythmia, characterization of arrhythmia and/or changes in heart rate. In an exemplary embodiment of the invention, heart rate is reduced as the contractility improves and each contraction delivers more blood to the body. Optionally, measured parameters indicate sympathetic and parasympathetic nervous activity.

Alternatively or additionally, oxygen and/or $CO_2$ consumption in the left ventricle can be measured, e.g. by infrared, as used oxygen saturation monitors.

Experimental Data

Referring now to FIGS. 3A, 3B, 3C and 3D, an exemplary demonstration that a mechanical activation profile according to the present invention can be employed to assess the influence on cardiac function (e.g. contractility) of an applied stimulus (e.g. CCM) is presented. The data is from an experiment conducted on a Pig in the animal facility of the Technion in Haifa Israel. The animal subject was fitted with an ECG monitor, a Millar catheter to measure intra-ventricular pressure, and an automated blood pressure cuff on a leg. The Millar catheter, ECG and blood pressure cuff were each provided with an interface to a computer which facilitated temporal registration of the three data sets.

Figure 3A:
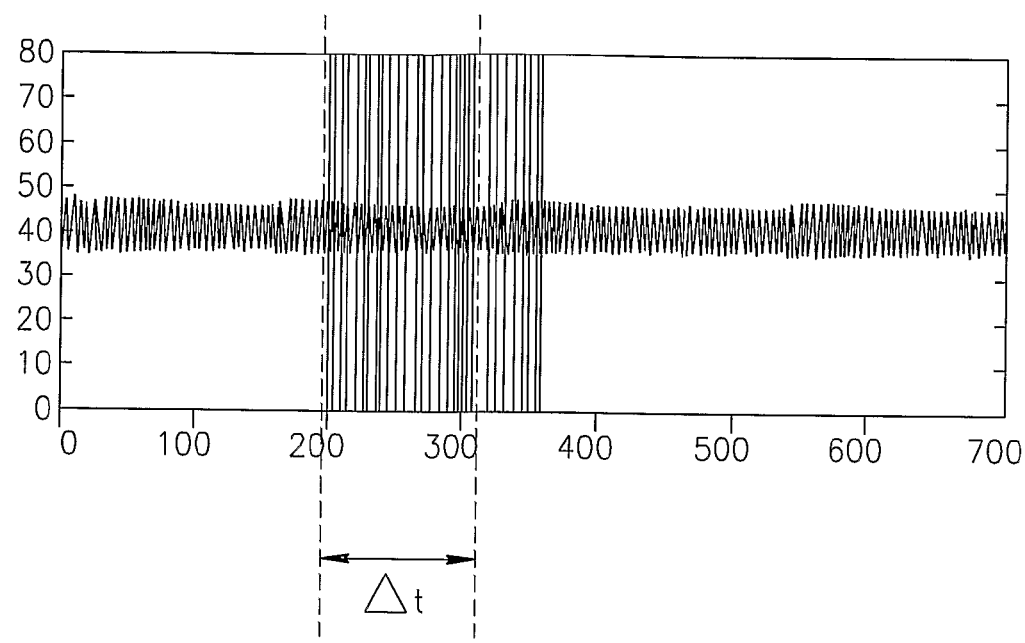
FIGS. 3A, 3B, 3C, 3D, are graphs of an ECG (including CCM artifacts), intra-cardiac pressure data reflecting an applied CCM signal, change in intra-cardiac pressure data as a CCM signal is applied and change in peripheral vascular pressure all plotted as a function of time according to an exemplary embodiment of the present invention, respectively.
Figure 3B:
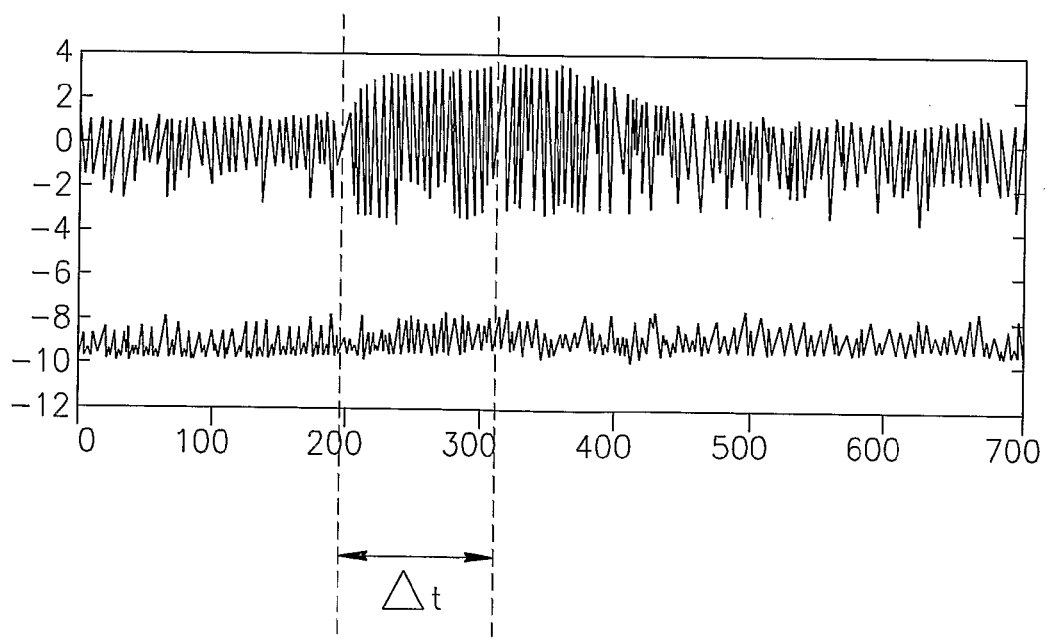

FIG. 3A is a plot of ECG data which illustrates interference caused by a CCM signal (high amplitude waves). FIG. 3B is a plot of raw intra-ventricular pressure data from the Millar catheter. The graph indicates a sharp increase in pressure shortly after the onset of CCM delivery.

Figure 3C:
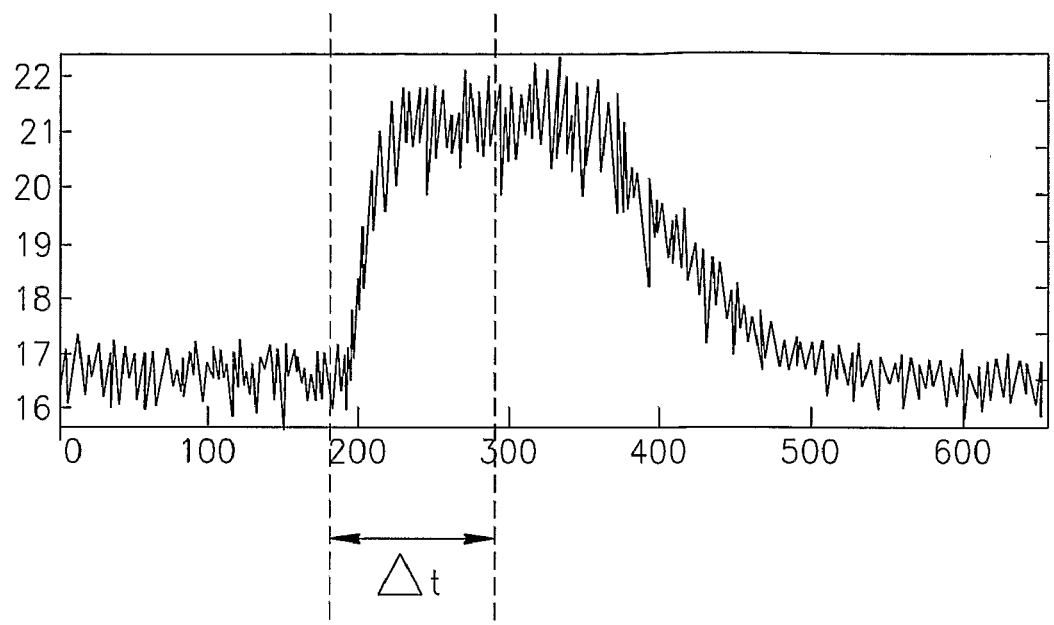

FIG. 3C is a plot of intra-ventricular max dP/dt as a function of time. Plotting the first derivative of pressure with respect to time highlights the time at which the onset of the pressure increase occurs.

Figure 3D:
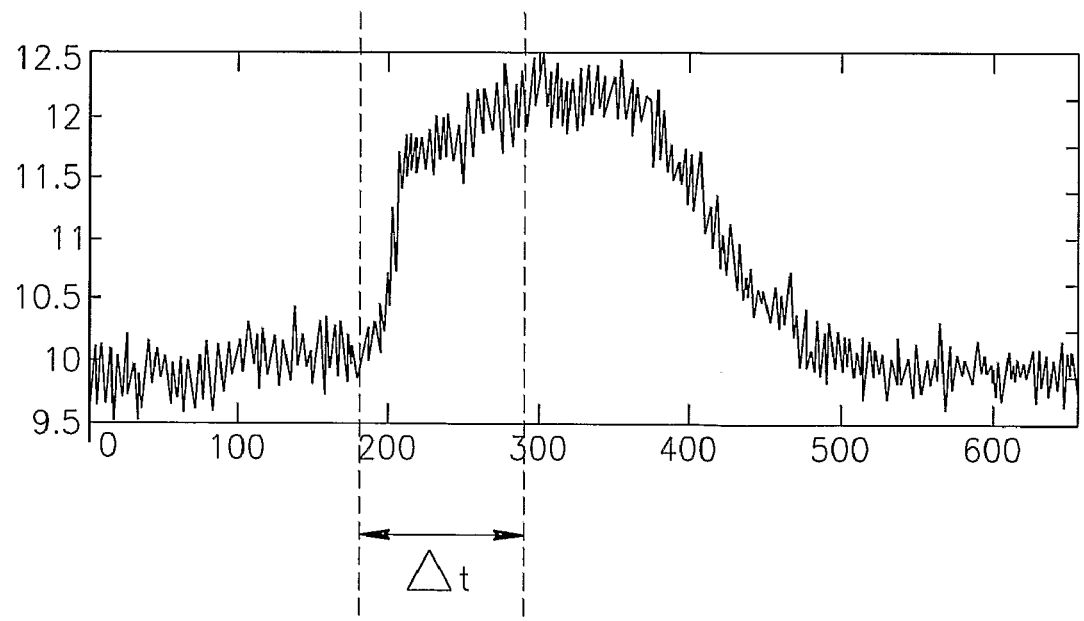

FIG. 3D is a plot of peripheral blood max dP/dt as a function of time. A good correlation between changes in peripheral blood pressure and intra-ventricular pressure is demonstrated. The presented graphs are representative of more than 20 repetitions of the experiment in a single animal.

The delay of tens of second (indicated as $\Delta t$) between the onset of CCM and the maximum elevation of max dP/dt indicates that there may be differences in interpretation of the phenomena, even though the phenomena clearly appears in the first few seconds. For example FIG. 3C and FIG. 3D show that the response is immediate and significant, yet, the measurement from the heart reaches plateau quickly, while measurement form the periphery continues to build up over prolonged period.

Data Manipulation

Because CCM causes unwanted interference in measurements, it is often desirable to clean, smooth or correct the data sets. This may be accomplished in a variety of ways. Exemplary methods of data manipulation are described hereinbelow for purposes of illustration only and should not be construed to limit the scope of the invention.

Figure 4:
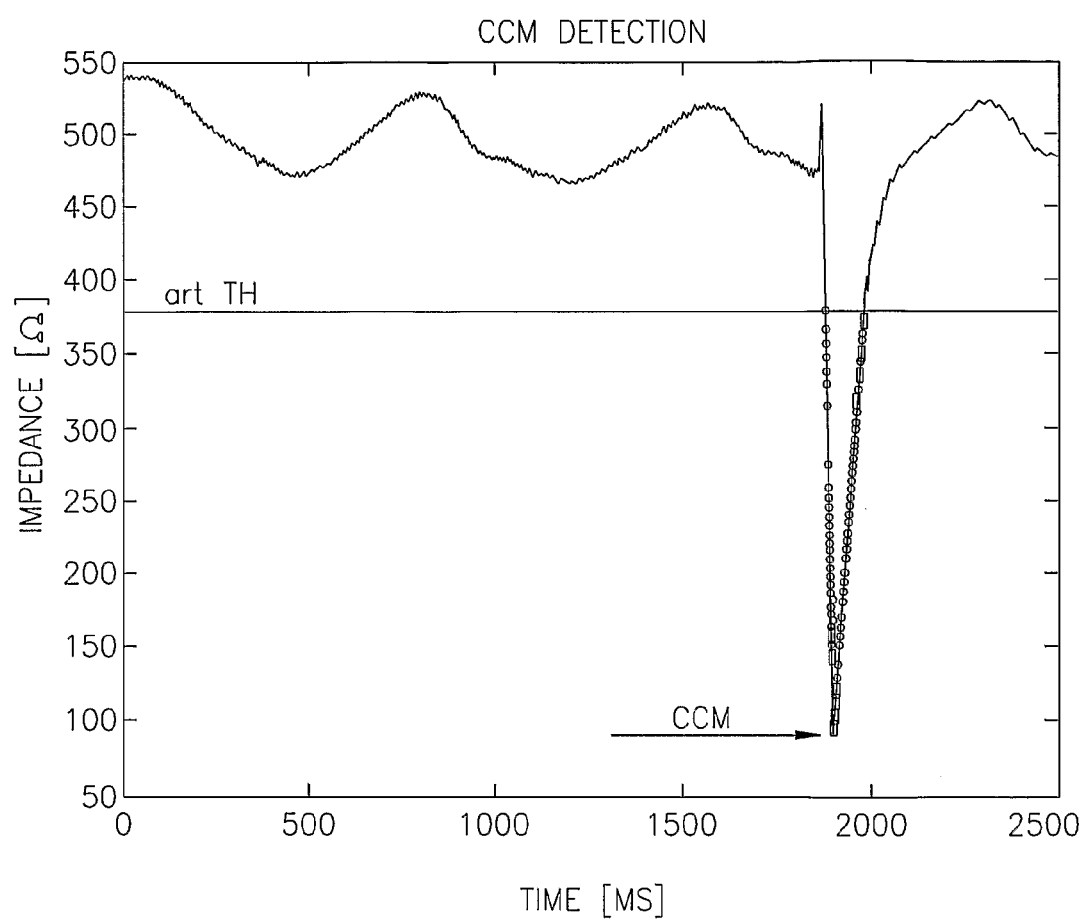
FIG. 4 is a graph illustrating that a CCM signal causes interference to an impedance measurement as a function of time, which would render portions of the plot unusable in the absence of the present invention.

Referring now to FIG. 4, a plot of impedance as a function of time data collected over N=2500 milliseconds is shown. The plot shows two full peak to peak cycles before the third cycle is interrupted by CCM delivery at about 1900 milliseconds. The impedance values are analyzed for the peak to peak cycle prior to the CCM delivery and an artifact threshold (artTH) is established.

The impedance channel is sorted in ascending order (SortZ=sort (z)). Calculation of peak to peak values ignoring margin values is performed as follows:

$$P2P=SortZ(round(0.9*N))-SortZ(round(0.4*N));$$

$$ZP2P=0.25*P2P+0.75*ZP2P; \text{ (adaptive update)}$$

Artifact samples are defined as:

$$artTH=(SortZ(round(0.9*N))-4*ZP2P);$$

$$\text{art points}=find(z<artTH);$$

The lowest point at each artifact samples group defines the CCM location (FIG. 4; indicated by arrow).

Figure 5A:
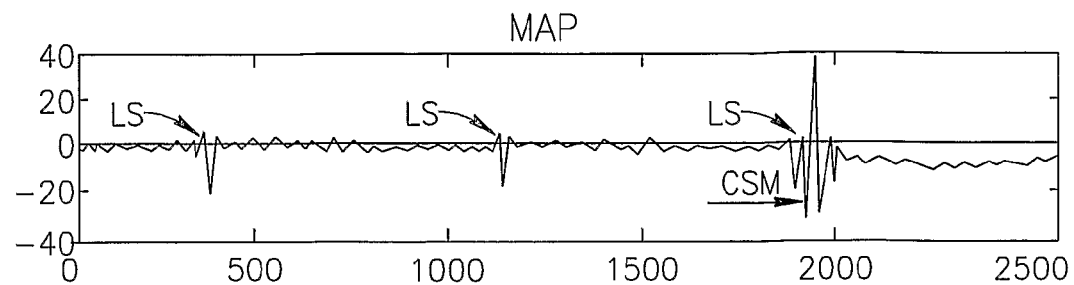
FIGS. 5A, 5B and 5C are graphs illustrating an ECG with CCM interference (5A) as a function of time, the same plot cleaned of CCM interference by an exemplary embodiment of the present invention (5B) and filtered according to an exemplary embodiment of the present invention with a band pass.
Figure 5B:
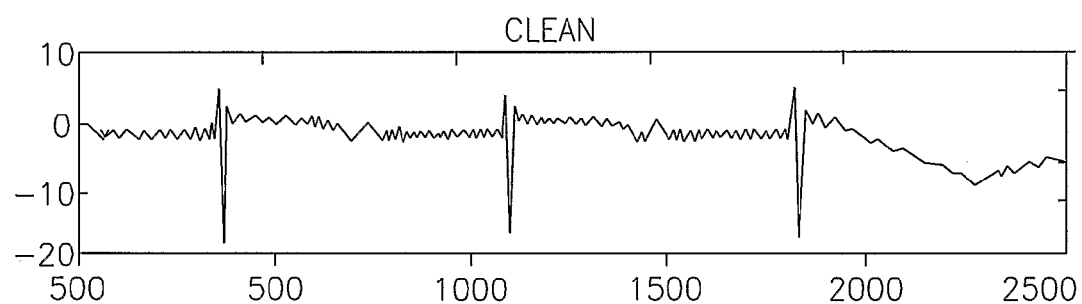
Figure 5C:
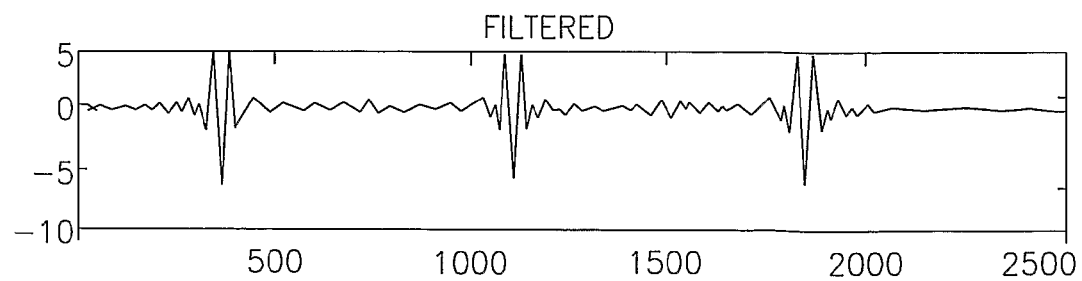

FIGS. 5A, 5B and 5C, FIG. 5A show a set of intracardiac ECG data collected over 2500 milliseconds (MAP). CCM location determined by the impedance channel as described hereinabove is superimposed on the MAP data (circle).

In order to clean the MAP data of CCM interference, the first sharp change in the signal before each CCM location is determined. Then a dT from the first sharp change before CCM location to CCM location is determined. A CleanBack step is performed by rounding (mean (dT))+10 and the region is interpolated by [CCM location−CleanBack: CleanBack+ 350 ms] to produce the Clean plot of FIG. 5B. Application of a band pass filter of 15-30 Hz produces the filtered plot of FIG. 5C.

Figure 6A:
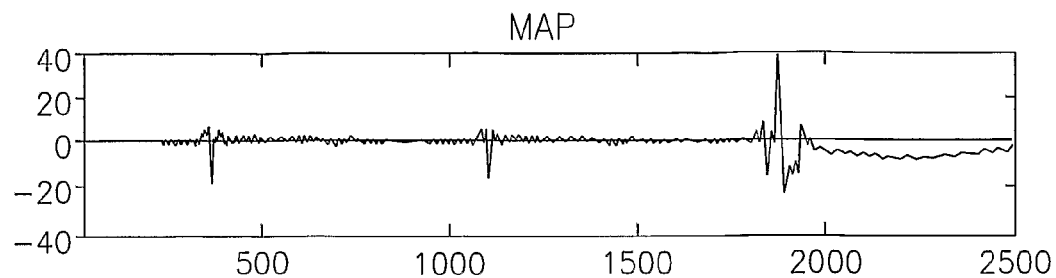
FIGS. 6A, 6B and 6C are graphs illustrating a Monophasic Action Potential (MAP) with CCM interference (6A), derivative of the MAP signal cleaned of CCM interference according to an exemplary embodiment of the present invention (6B) and abs MAP (6C) all as a function of time according to an exemplary embodiment of the present invention.
Figure 6B:
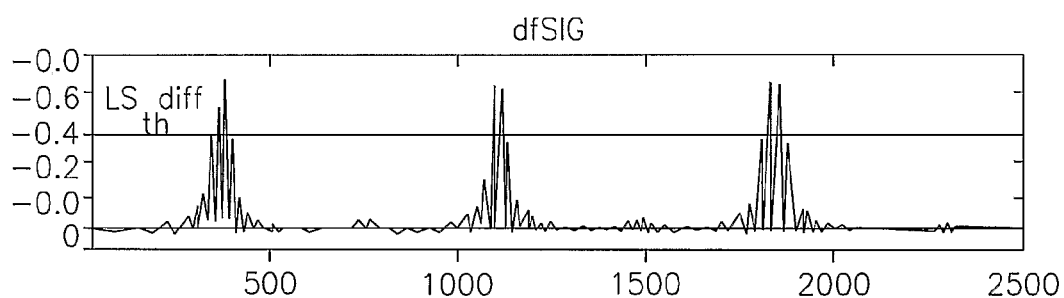
Figure 6C:
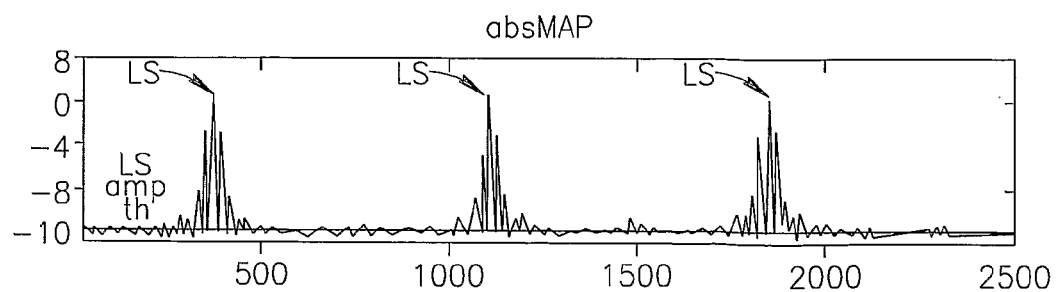

FIGS. 6A, 6B and 6C show a set of intracardiac ECG data collected over 2500 milliseconds (6A; MAP). CCM location determined by the impedance channel as described hereinabove is superimposed on the MAP data. The absolute value of the derivative as calculated by abs (diff (Fsig)) is presented in FIG. 6B (dFsig). FIG. 6C shows absMAP data with local sense (LS) candidates determined by threshold crossing of dFsig. LS is defined as local maxima of absMAP in the range of [candidates−100 ms: candidates+50]. Adaptive thresholds LS_diff_th, LS_amp_th are updated in accord.

In an additional exemplary embodiment of the invention, calculation of the LS is by finding the center of mass in the square of dFsig around the points that passed the threshold LS_diff_th. This calculation is optionally employed when there is more than one local maxima with almost the same amplitude.

Figure 7:
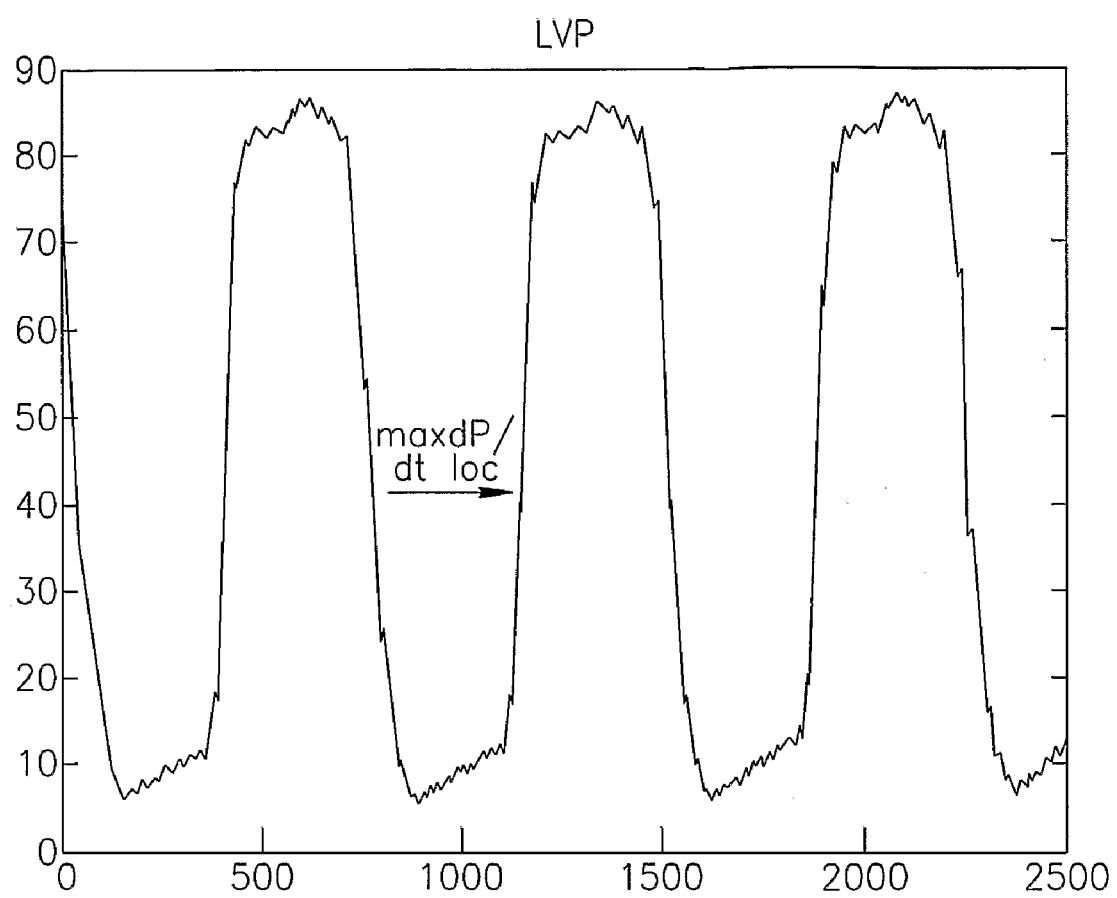
FIG. 7 is a graph of left ventricular pressure (LVP) as a function of time illustrating the cyclic nature of LVP and the max dP/dt upon which some embodiments of the present invention rely.

FIG. 7 is a plot of Left Ventricle pressure as a function of time over 2500 milliseconds. A 30 Hz low pass filter has been applied. Using LS and CCM location as determined above, the maximum dP/dt location (indicated by an arrow) is calculated by finding the maximum of (X10(x1−10))/10 around LS.

Figure 8A:
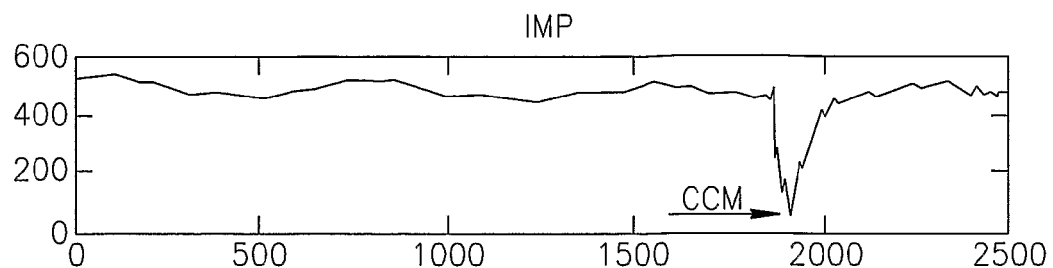
FIGS. 8A, 8B and 8C are graphs illustrating impedance measurements with CCM interference (8A), the same plot with artifact removed (8B) by an exemplary embodiment of the present invention and filtered with a band pass filter, all as a function of time according to an exemplary embodiment of the present invention.
Figure 8B:
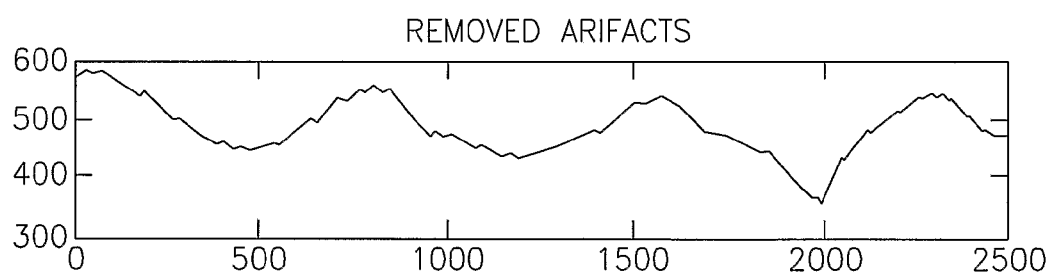
Figure 8C:
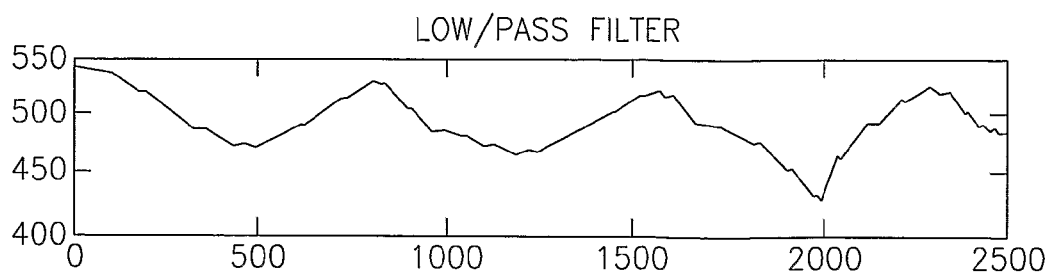

FIGS. 8A, 8B and 8C are graphs of impedance as a function of time for 2500 milliseconds with CCM location and LS superimposed is presented (8A; IMP). FIG. 8B (removed artifacts) shows the same data with artifacts at CCM location ±80 milliseconds replaced with interpolated values. FIG. 8C shows the plot of FIG. 8B with a low pass filter of 30 Hz to 50 Hz applied.

Figure 9:
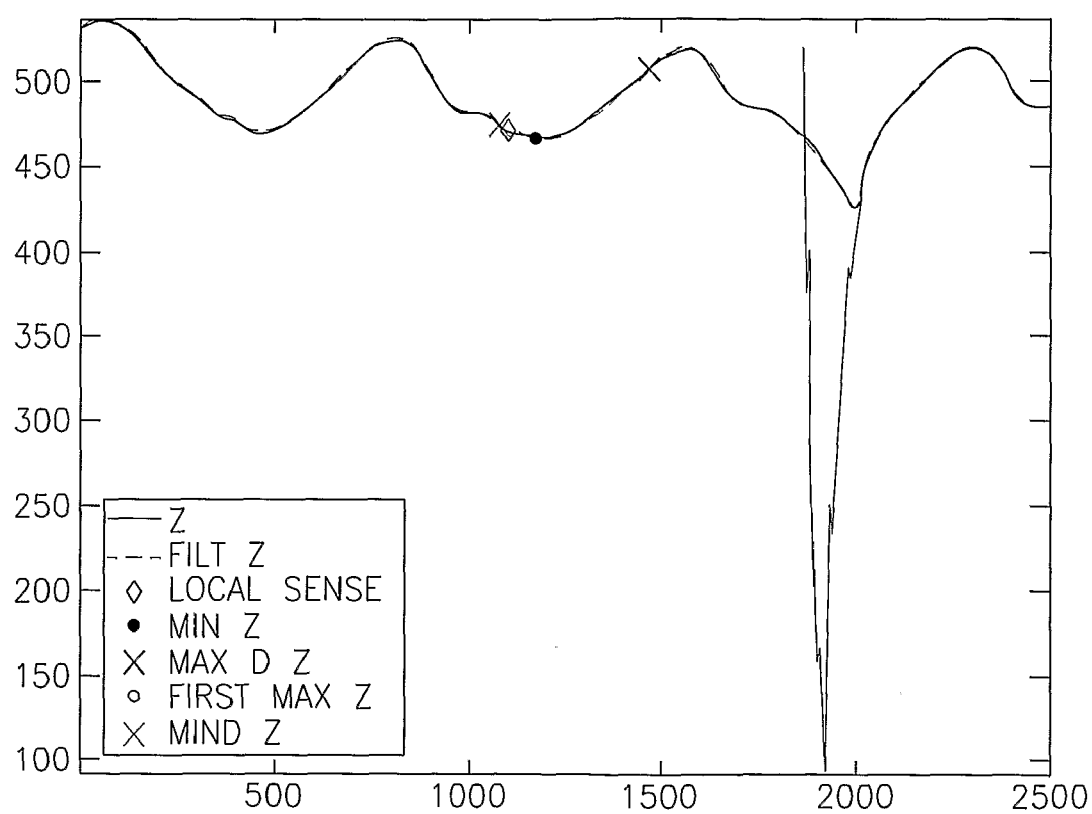
FIG. 9 is a graph illustrating temporal position of important cardiac events as determined by various embodiments of the present invention overlaid on impedance as a function of time with interference from a CCM signal clearly visible as presented in FIG. 4.

FIG. 9 is similar to FIG. 4, but indicates min (Z), max (dZ), max (Z), min (dZ) and their distance from LS where Z indicates impedance. These calculations exemplify the utility of the present invention in establishing a correlation between mechanical events (e.g. contractility) and non mechanical measurement parameters (e.g. pressure and/or impedance)

Prediction Models

Parameters determined as detailed with reference to FIGS. 4 through 9 may be predictive to contractility changes of the left ventricle (LV). Optionally, the parameters are measured and compared to their baseline values. Optionally, the baseline value is taken as the average value of the measured parameter during one minute before the beginning of CCM activation.

For example, a change in LV contractility may be measured by:
1. max dP/dt;
2. Time shortening during isovolumetric period can be measured by the following periods:
   a. min(Z) time−LS time
   b. max(Z) time−LS time
   c. max(dZ) time−LS time
   d. Other ratios and relations among the above and among the information from other leads
3. Approximation of ejection fraction (EF) from the impedance parameters:
   Cs=approximated conductance during systole.
   Cd=approximated conductance during diastole.
   RelChange=(Cd−Cs)/Cd;
   M=0.2
   α=1−DS_RelChange.*(1+M)
   EF=1−α³

During CCM activation the CCM artifact starts after the local sense (LS) and hides the location of min (Z) and max (dZ).

In an exemplary embodiment of the invention, the problem caused by the CCM artifact is overcome by imposing a duty cycle on the CCM signal (e.g. 3 out of four beats (3/4) or other duty cycles 6/8, 7/8). Optionally, comparison with the baseline is only conducted on beats in which no CCM signal is delivered. These beats are not affected by a CCM artifact. In an exemplary embodiment of the invention, an established effect of CCM persists during those beats in the duty cycle in which CCM is not applied.

In an exemplary embodiment of the invention, the problem caused by the CCM artifact is overcome by using a polynomial approximation. Optionally, a polynomial approximation of order 5 or higher is employed to approximate the beat ignoring the artifact period. Desired features may then be extracted from the estimated signal.

In some cases, respiration may interfere with collected data and/or extracted features. In order to reduce respiration interference, data and/or extracted features can be analyzed after averaging several beats. In an exemplary embodiment of the invention, each analyzed beat on the impedance channel is an average region of 1000 ms of the previous 20 beats, where each beat is synchronized to the local sense.

Some methods and apparatus according to the present invention rely upon execution of various data measurements, commands and analysis and translation of various data inputs. Any of these commands, analyses or translations may be accomplished by software, hardware and/or firmware according to various embodiments of the invention. In an exemplary embodiment of the invention, machine readable media contain instructions for commands and/or analyses and/or translations. In an exemplary embodiment of the invention, circuitry, for example an ASIC device and/or a computer executes instructions for data acquisition and/or data translation and/or data correlation and/or analysis.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features, shown in a particular described exemplary embodiment. Alternatively or additionally, portions of the invention described/depicted as a single unit may reside is two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. In particular, features described in the context of a method may be incorporated into a device or system. The scope of the invention is limited only by the following claims.

All publications and/or patents and/or product descriptions cited in this document are fully incorporated herein by reference to the same extent as if each had been individually incorporated herein by reference.

The invention claimed is:

1. A method of assessing efficacy of a treatment on cardiac contractility, the method comprising:
   (a) utilizing time correlated data pertaining to an activation parameter, to produce a first profile of said parameter, comprising:
      (i) measuring at least one parameter as a function of time to generate a cardiac activation profile;
      (ii) identifying from the measurement of said at least one parameter a time interval during which interference from an artificial signal occurs; and
      (iii) ameliorating effects of said interference;
   (b) analyzing changes in said first profile to generate an indication of contractility;
   (c) applying a treatment and re-performing steps (a) and (b) to generate a second profile; and
   (d) comparing said first profile and said second profile to ascertain an efficacy of the treatment.

2. A method according to claim 1, wherein said activation parameter includes a mechanical activation parameter.

3. A method according to claim 2, wherein said mechanical activation parameter includes at least one of impedance and acoustic output.

4. A method according to claim 1, wherein said analyzing changes includes analyzing changes in a first derivative of the profile.

5. A method according to claim 1, wherein said time correlated data is acquired without any intra-corporeal measuring device.

6. The method of claim 1, wherein said treatment includes administration of a cardiac contractility modulation (CCM) input.

7. A method according to claim 1, additionally comprising analyzing said activation parameter correlated to time and said corresponding CCM input.

8. A method according to claim 7, wherein said analyzing further comprises providing an output in the form of a desired change in activation profile.

9. A method according to claim 7, wherein said analyzing further comprises providing an output in the form of a recommended change in CCM delivery.

10. A method according to claim 9, wherein said a controller implements the recommended change in CCM delivery.

11. A method according to claim 1, wherein said ameliorating includes data deletion followed by interpolation to reconstruct a missing portion of said profile.

12. A method according to claim 1, wherein said ameliorating includes data deletion followed by data regeneration to reconstruct a missing portion of said profile.

13. A method according to claim 1, wherein said amelioration includes application of a band pass filter.

14. The method of claim 1, wherein said treatment includes administration of an electric signal.

15. A method according to claim 1, wherein said ameliorating comprises modifying an application of said artificial signal during said measuring.

16. A method according to claim 15, wherein said modifying comprises changing one or more of a time, application electrodes, amplitude and frequency of said artificial signal.

17. A method according to claim 16, wherein ameliorating comprises changing application electrodes and wherein said application electrodes are selected to be distanced from a measuring location of said measuring.

18. A method according to claim 16, wherein application electrodes are changed between beats to allow measurement at multiple locations.

19. A method according to claim 1, wherein ameliorating comprises ameliorating using data from other beats.

20. A method according to claim 19, wherein ameliorating comprises averaging for different artificial signal applications.

21. A method according to claim 1, wherein ameliorating comprises measuring an effect of the signal in a beat after the artificial signal is applied and stopped.

22. A method according to claim 1, further comprising turning off a measuring system during an application or expected application of said artificial signal.

23. A method according to claim 1, wherein ameliorating comprises reconstructing missing peak data.

24. A method according to claim 23, wherein the missing data is reconstructed based on a slope of the peak.

25. A method according to claim 23, wherein the missing data is reconstructed based on a relaxation time of the peak.

26. A method according to claim 23, wherein a peak decay is reconstructed based on a peak rise or a peak rise is reconstructed based on a peak decay.

27. A method according to claim 1, wherein ameliorating comprises reconstructing missing data using data from times outside the time of application of the artificial signal, using fitting or interpolation.

28. A method according to claim 1, wherein said artificial signal is applied during a refractory period of said the heart being measured.

29. A method according to claim 1, wherein said artificial signal is applied for a period of at least 10 milliseconds long during which said measurement is compromised and later ameliorated.

30. A method according to claim 1, wherein said artificial signal is applied for a period of at least 20 milliseconds long during which said measurement is compromised and later ameliorated.

31. A method according to claim 1, further comprising identifying a sharp change in said at least one parameter.

32. A method according to claim 1, further comprising identifying a slope above a certain threshold in said at least one parameter.

33. A method according to claim 1, further comprising identifying a value over a certain threshold in said at least one parameter.

34. A method according to claim 1, wherein said identifying comprises identifying an interference which occurred.

35. A method according to claim 1, wherein said measurement of said at least one parameter is used to predict when an interference will occur.

36. A method according to claim 1, additionally comprising displaying the values of said activation parameters correlated to time as an activation profile.

37. The method of claim 1, wherein said artificial signal results from pacing.

38. The method of claim 1, wherein said artificial signal results from a CCM delivery.

39. A method of positioning a lead, the method comprising,
(a) utilizing time correlated data pertaining to an activation parameter, to produce a first profile of said parameter, comprising:
   (i) measuring at least one parameter as a function of time to generate a cardiac activation profile;
   (ii) identifying from the measurement of said at least one parameter a time interval during which interference from an artificial signal occurs; and
   (iii) ameliorating effects of said interference;
(b) analyzing changes in said first profile to generate an indication of contractility;
(c) applying a therapeutic signal through a lead at a position in said heart at a known time;
(d) performing a method according to steps (a) and (b) to generate a second profile;
(e) comparing said first and second profile; and
(f) adjusting the positioning of the lead responsive to said comparison results.

40. A method according to claim 39, wherein adjusting the positioning of the lead responsive to comparison results comprises adjusting if a selected portion of said first profile is not significantly narrower in said second profile.

41. A method according to claim 39, wherein said therapeutic signal is a pacing signal.

42. A method according to claim 39, wherein said applying a signal comprises applying a non excitatory signal.

43. A method according to claim 42 wherein the non-excitatory electric therapy includes CCM.

44. A method according to claim 39, wherein a significant narrowing in said profile indicates that said position is said desired position.

45. A method of generating a profile of the heart, the method comprising:
(a) measuring at least one parameter as a function of time to generate a cardiac activation profile;
(b) identifying from the measurement of said at least one parameter a time interval during which interference from an artificial signal occurs; and
(c) ameliorating effects of said interference;
wherein:
said amelioration includes calculation of a first derivative of said function.

46. A method of assessing efficacy of a non-excitatory electric treatment, the method comprising:
(a) performing a method to generate a first profile, said method comprising:
   (i) utilizing time correlated data pertaining to an activation parameter measured by:
      (A) measuring at least one parameter as a function of time to generate a cardiac activation profile;
      (B) identifying from the measurement of said at least one parameter a time interval during which interference from an artificial signal occurs; and
      (C) ameliorating effects of said interference;
   to produce a profile of said parameter; and
   (ii) analyzing changes in said profile to generate an indication of therapy efficacy;
(b) applying a treatment and re-performing a method according to step (a) to generate a second profile;
(c) comparing said first profile and said second profile to ascertain an efficacy of the treatment.

47. A method according to claim 46, wherein said activation parameter includes a mechanical activation parameter.

48. A method according to claim 46 wherein the non-excitatory electric treatment includes CCM.

49. A method of assessing cardiac disease progression in a subject, the method comprising:
(a) generating a first profile by:
   (i) utilizing time correlated data pertaining to an activation parameter measured by:
      (A) measuring at least one parameter as a function of time to generate a cardiac activation profile;
      (B) identifying from the measurement of said at least one parameter a time interval during which interference from an artificial signal occurs; and
      (C) ameliorating effects of said interference;
   to produce a profile of said parameter; and
   (ii) analyzing changes in said profile to generate an indication of therapy efficacy;
(b) allowing an increment of time to elapse and re-performing a method according to step (a) to generate a second profile;
(c) comparing said first profile and said second profile to ascertain a degree of disease progression.

* * * * *